United States Patent
Griffin et al.

(10) Patent No.: US 12,075,826 B2
(45) Date of Patent: Sep. 3, 2024

(54) VAPORIZER APPARATUSES HAVING A MOVABLE HEAD AND RELATED METHODS

(71) Applicant: Furna Inc., Kitchener (CA)

(72) Inventors: Jason Griffin, Kitchener (CA); Steven Fyke, Kitchener (CA); Tim Mackay, Kitchener (CA); Bryan Cunningham, Edmonton (CA); Tyler Kibler, Edmonton (CA); Trevor Dix, Edmonton (CA)

(73) Assignee: Furna Inc., Kitchener (CA)

( * ) Notice: Subject to any disclaimer, the term of this patent is extended or adjusted under 35 U.S.C. 154(b) by 710 days.

(21) Appl. No.: 17/267,591

(22) PCT Filed: Aug. 9, 2019

(86) PCT No.: PCT/CA2019/051093
§ 371 (c)(1),
(2) Date: Feb. 10, 2021

(87) PCT Pub. No.: WO2020/142826
PCT Pub. Date: Jul. 16, 2020

(65) Prior Publication Data
US 2021/0307388 A1    Oct. 7, 2021

Related U.S. Application Data

(60) Provisional application No. 62/717,453, filed on Aug. 10, 2018, provisional application No. 62/717,479, filed on Aug. 10, 2018.

(51) Int. Cl.
*A24F 40/40*    (2020.01)
*A24F 7/02*    (2006.01)
(Continued)

(52) U.S. Cl.
CPC .............. *A24F 40/40* (2020.01); *A24F 7/02* (2013.01); *A24F 40/49* (2020.01);
(Continued)

(58) Field of Classification Search
CPC .. A24F 40/40; A24F 7/02; A24F 40/49; A24F 40/10; A61M 15/0021;
(Continued)

(56) References Cited

U.S. PATENT DOCUMENTS 6,196,232 B1    3/2001    Chkadua
9,877,520 B2 *    1/2018    Rastogi ..................... E05C 1/08
(Continued)

FOREIGN PATENT DOCUMENTS

WO    2013147492 A1    10/2013
WO    2017102686 A1    6/2017
(Continued)

OTHER PUBLICATIONS

Extended European Search Report in European Application No. 19909056.4 mailed Apr. 26, 2022, 7 pages.
(Continued)

*Primary Examiner* — Justin M Kratt
(74) *Attorney, Agent, or Firm* — Smith Baluch LLP

(57) ABSTRACT

Vaporizer apparatuses having a head movable between operational and non-operational positions are provided. The vaporizer apparatus comprises a body and the head. The head comprises a mouthpiece portion and is engaged with the body in the operational and non-operational positions. The apparatus further comprises a vaporizing chamber and vaporizing element operatively coupled to the vaporizing chamber and operable to vaporizing the material therein when activated. The vaporizing element is activatable when the head is in the operational position. The vaporizer apparatus may not be usable to vaporize the material when the (Continued)

head is in the non-operational position. Methods of providing vaporizer apparatuses having a head movable between operational and non-operational positions are also provided.

11 Claims, 30 Drawing Sheets

(51) Int. Cl.
*A24F 40/49* (2020.01)
*A61M 15/00* (2006.01)
*H05B 1/02* (2006.01)
*H05B 3/06* (2006.01)
*H05B 3/44* (2006.01)

(52) U.S. Cl.
CPC .... *A61M 15/0021* (2014.02); *A61M 15/0023* (2014.02); *H05B 1/0297* (2013.01); *H05B 3/06* (2013.01); *H05B 3/44* (2013.01); *A61M 15/0025* (2014.02); *A61M 15/0026* (2014.02); *H05B 2203/021* (2013.01)

(58) Field of Classification Search
CPC .......... A61M 15/0023; A61M 15/0025; A61M 15/0026; H05B 1/0297; H05B 3/06; H05B 3/44; H05B 2203/021
See application file for complete search history.

(56) References Cited

U.S. PATENT DOCUMENTS

| 9,999,245 | B1 | 6/2018 | Zhu |
| 2014/0334804 | A1 | 11/2014 | Choi |
| 2015/0157056 | A1 | 6/2015 | Bowen et al. |
| 2017/0099877 | A1* | 4/2017 | Worm ..................... A24F 40/70 |
| 2017/0150753 | A1 | 6/2017 | Macko |
| 2018/0027885 | A1 | 2/2018 | Qiu |
| 2018/0360125 | A1 | 12/2018 | James et al. |

FOREIGN PATENT DOCUMENTS

| WO | 2017102969 A1 | 6/2017 |
| WO | 2019129866 A1 | 7/2019 |
| WO | 2019154811 A1 | 8/2019 |
| WO | 2019186147 A1 | 10/2019 |

OTHER PUBLICATIONS

International Search Report and Written Opinion in International Patent Application No. PCT/CA2019/051093 mailed Sep. 19, 2019, 10 pages.

Extended European Search Report in European Application No. 20902859.6 dated Dec. 1, 2023 10 pages.

* cited by examiner

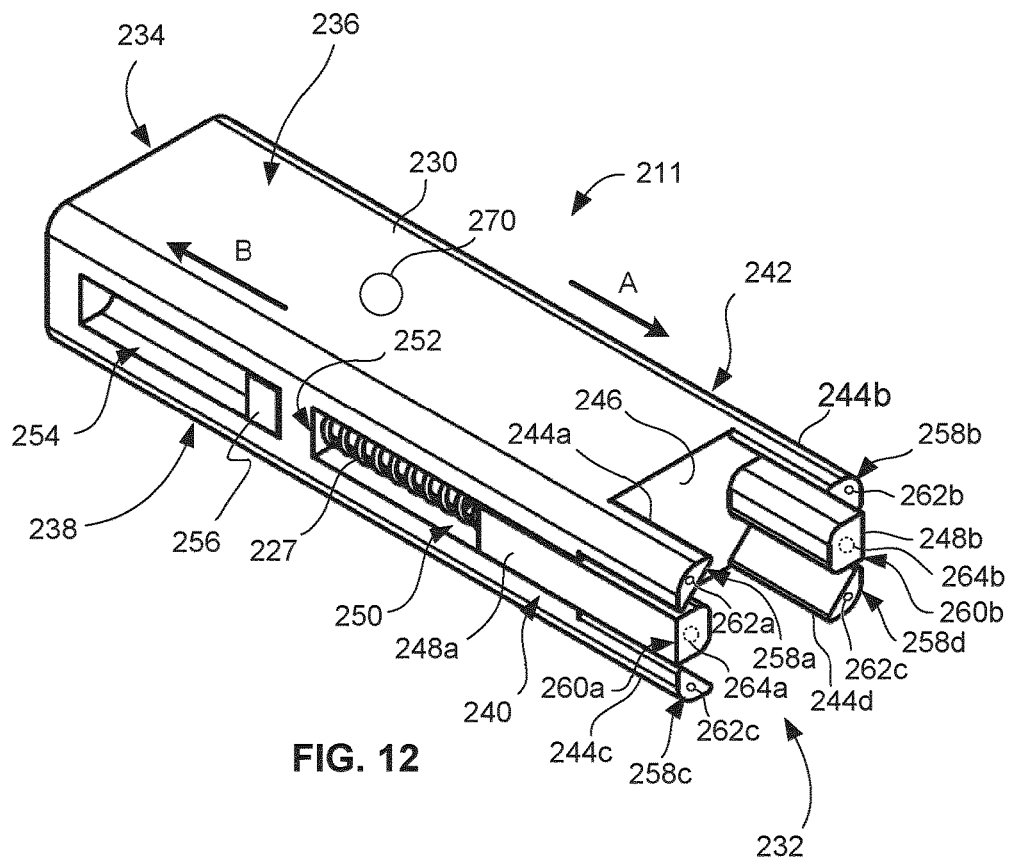
FIG. 12
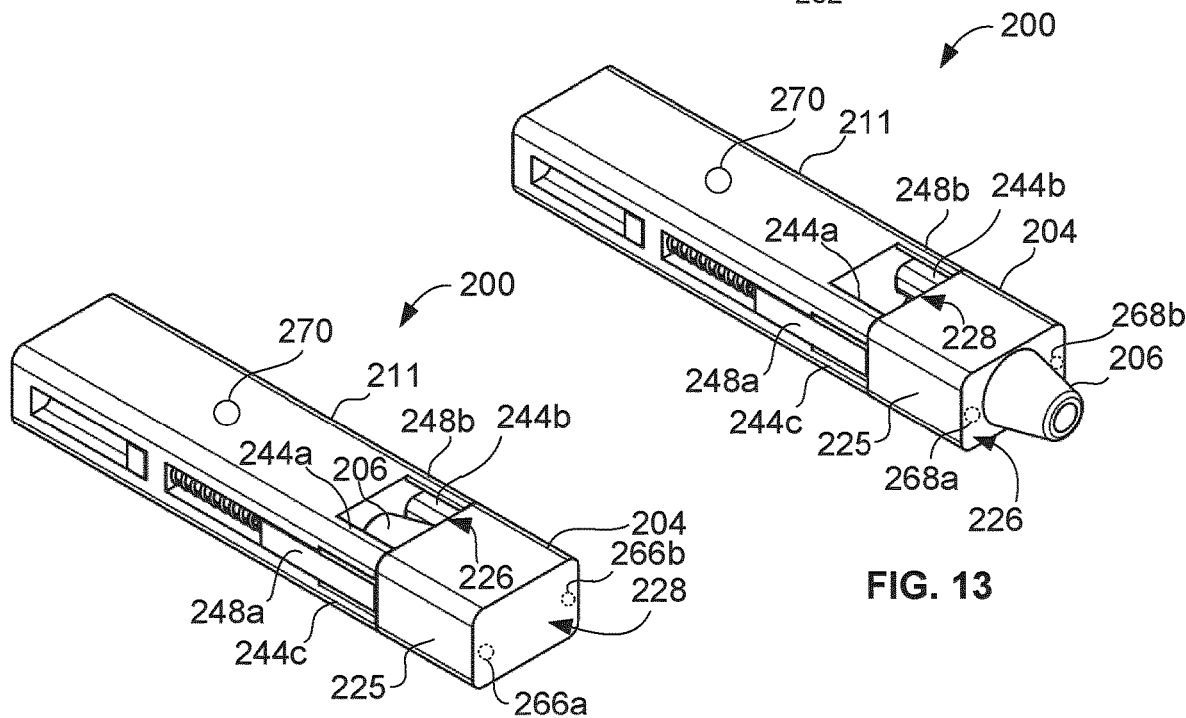
FIG. 13
FIG. 14

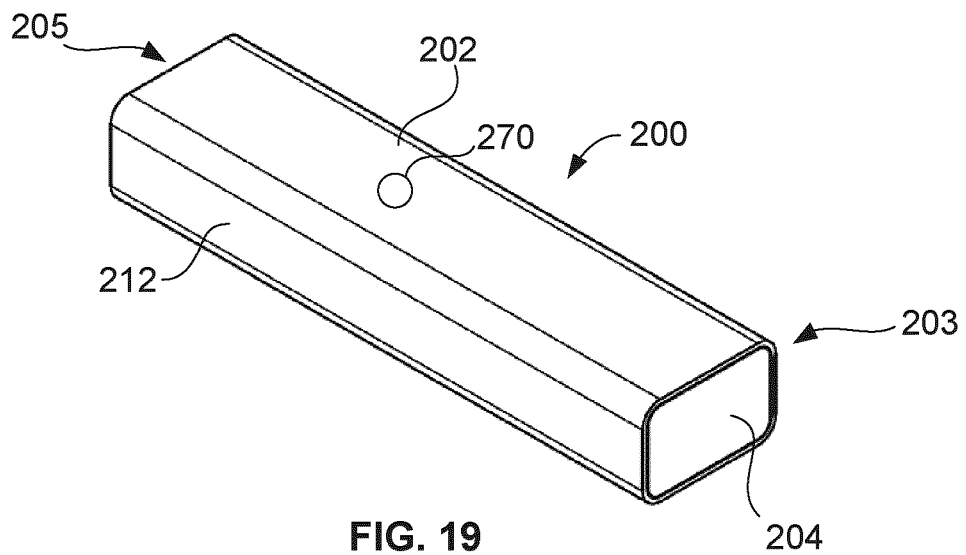
FIG. 19
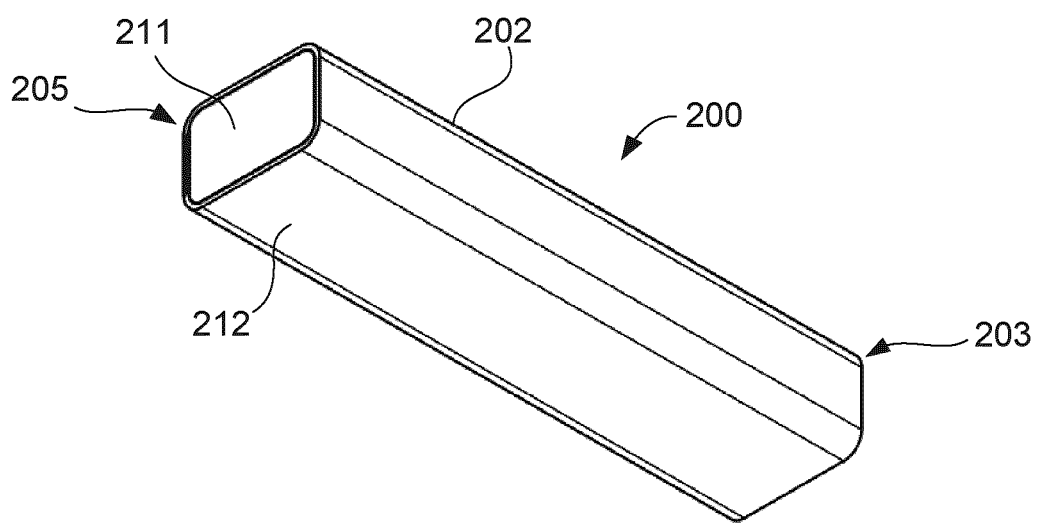
FIG. 20
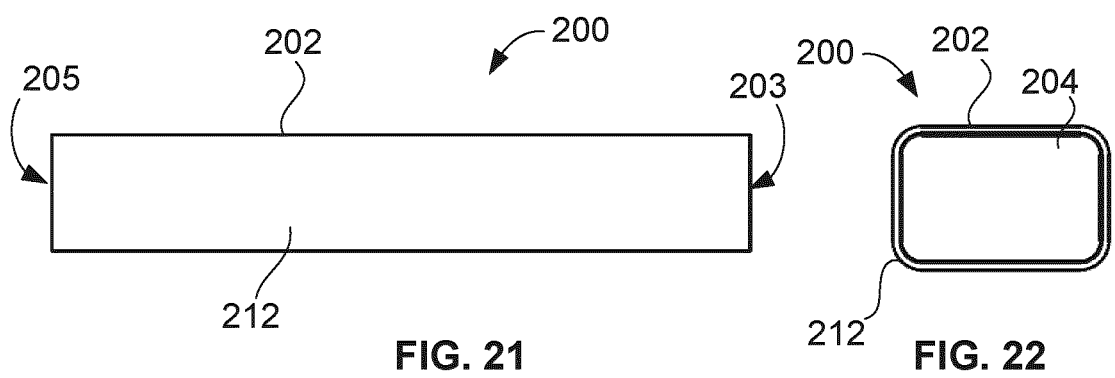
FIG. 21  FIG. 22

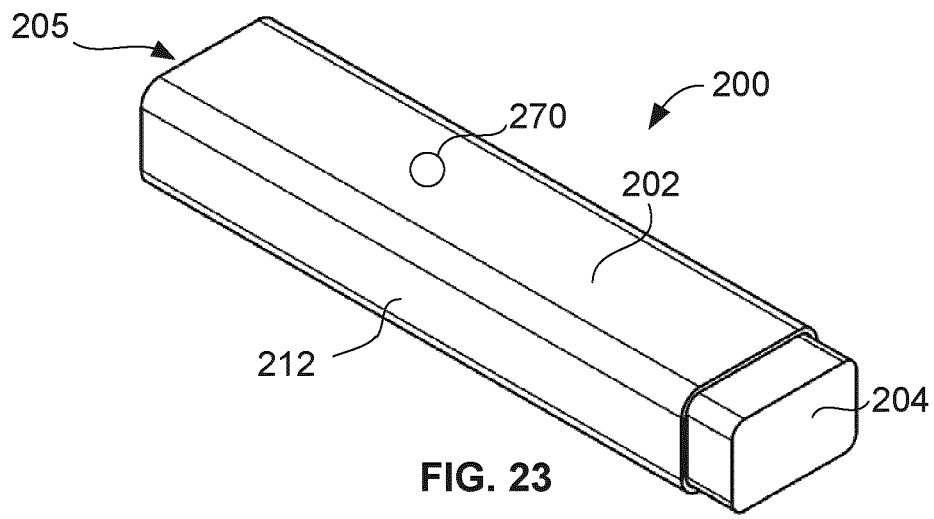
FIG. 23
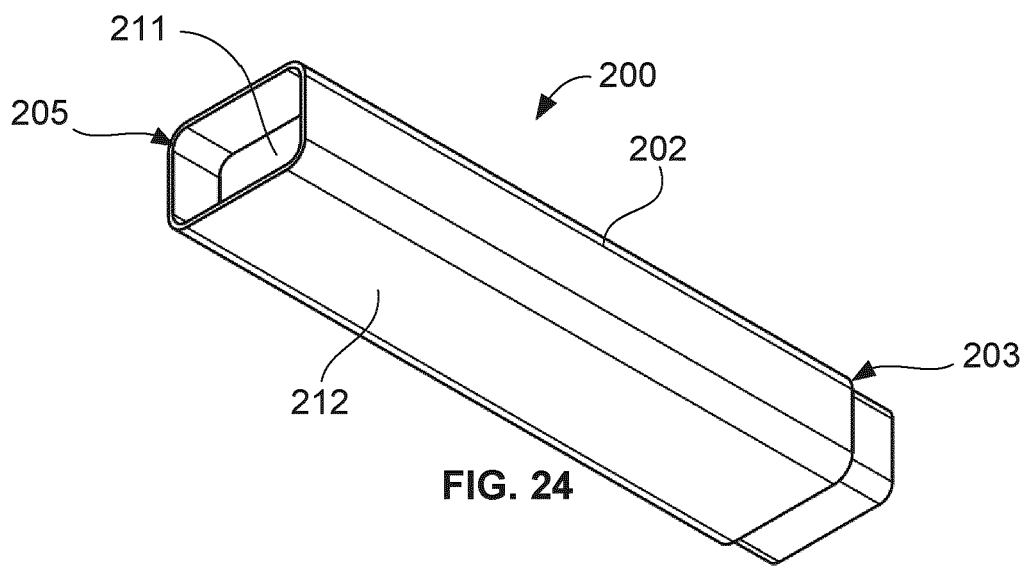
FIG. 24
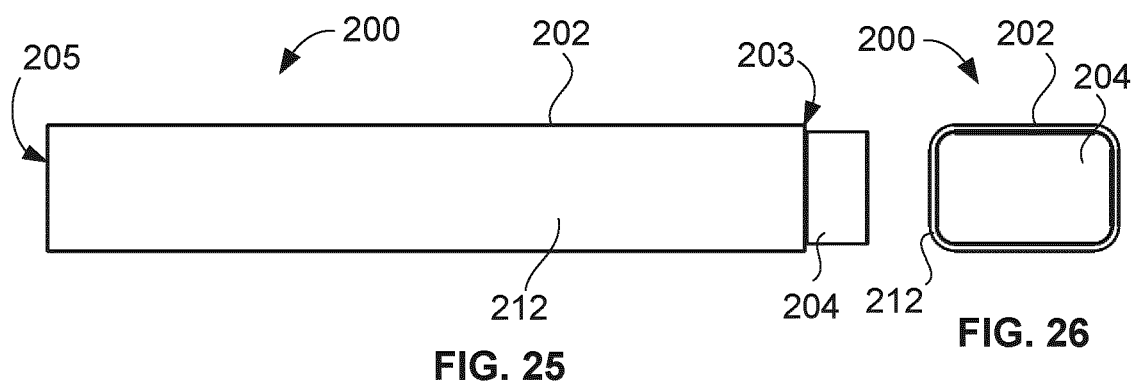
FIG. 25
FIG. 26

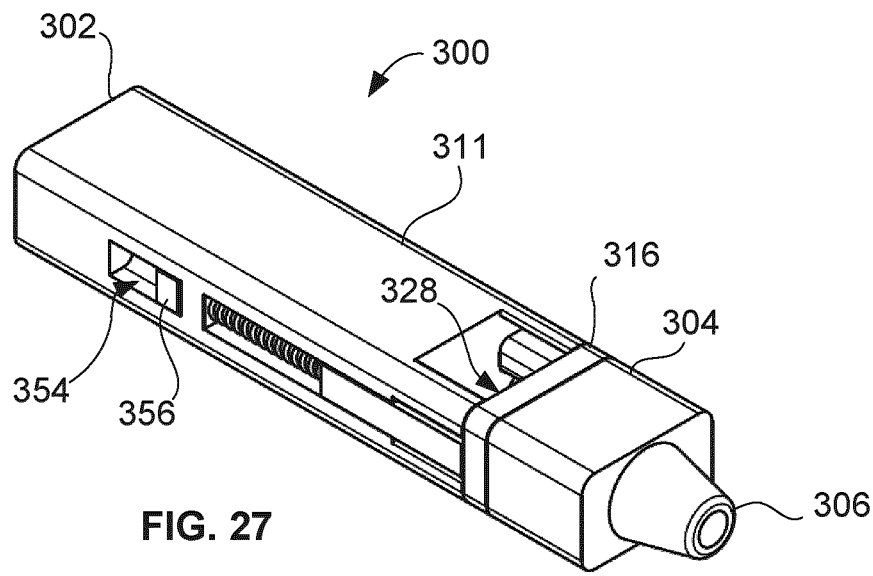
FIG. 27
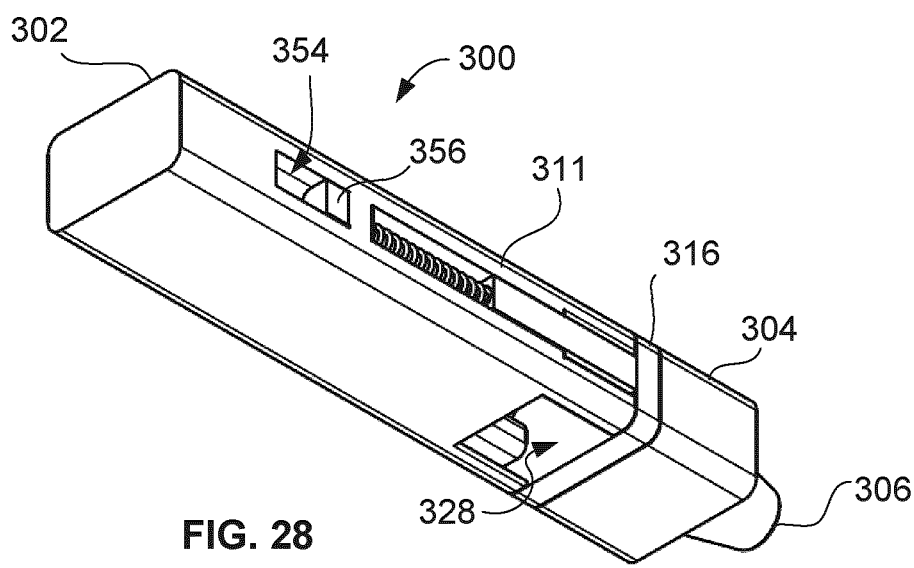
FIG. 28
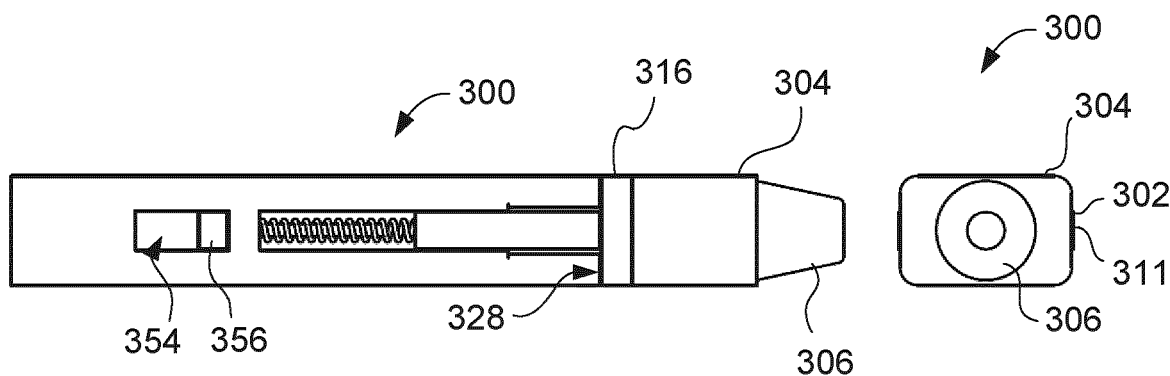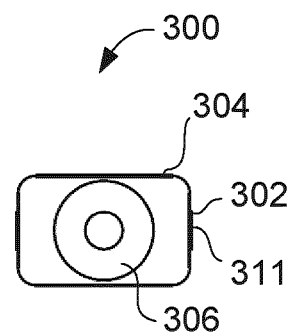
FIG. 29  FIG. 30

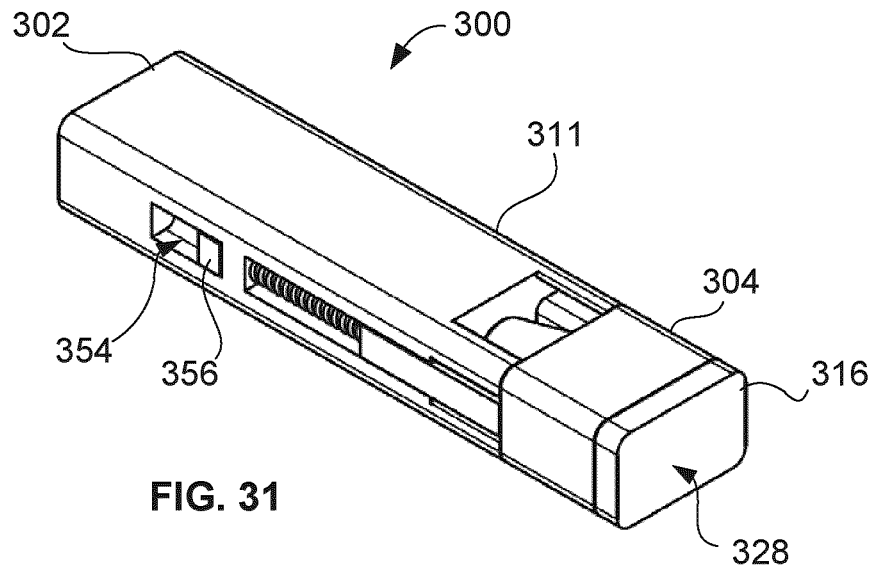
FIG. 31
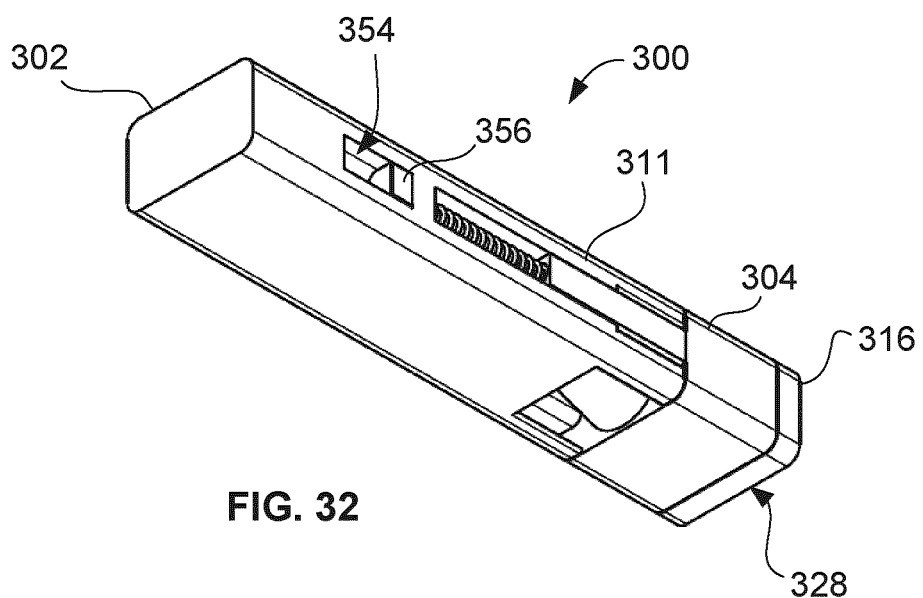
FIG. 32
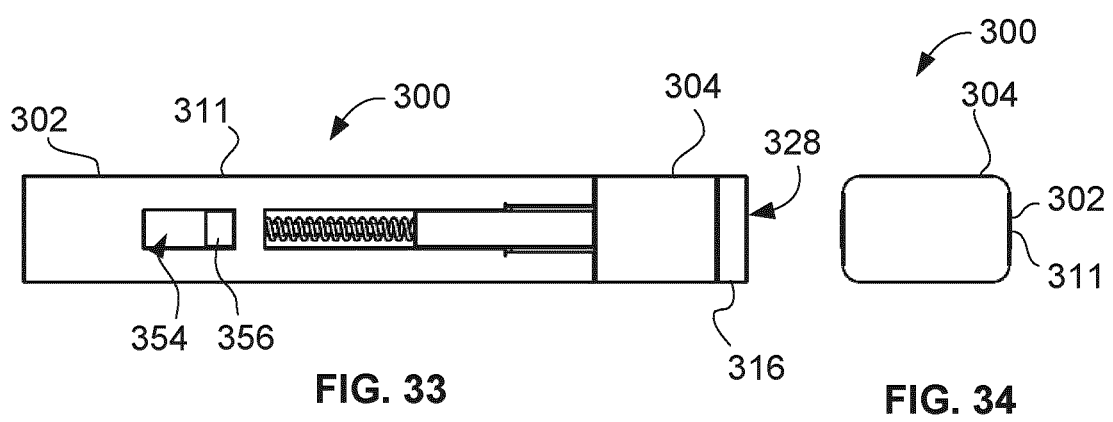
FIG. 33
FIG. 34

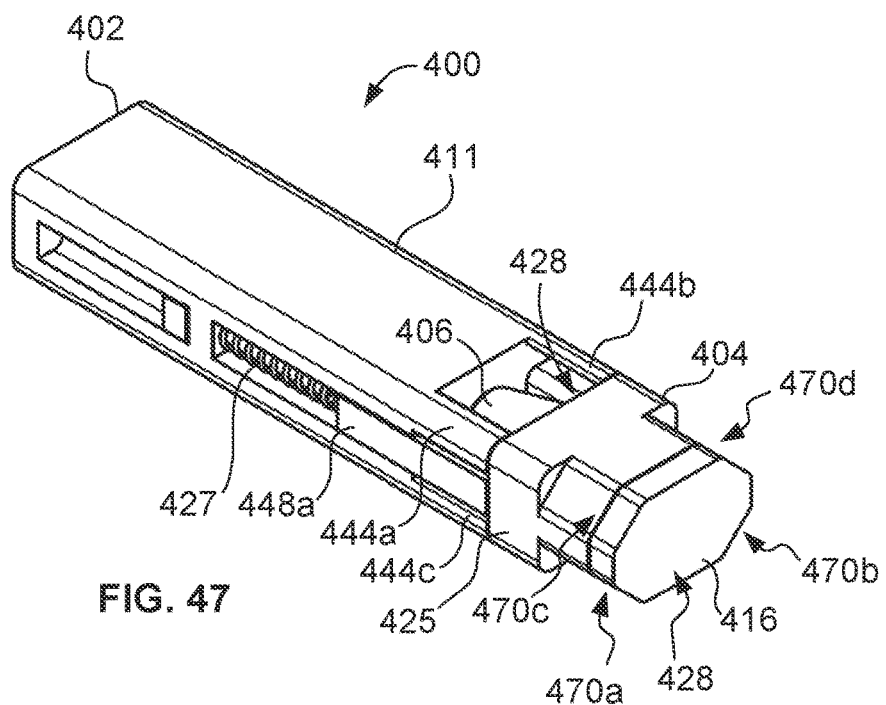
FIG. 47
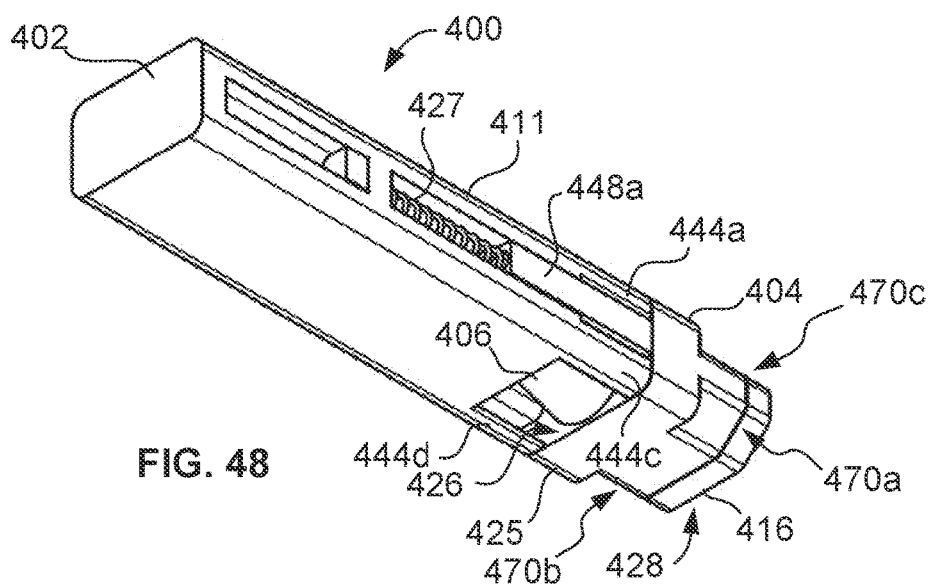
FIG. 48
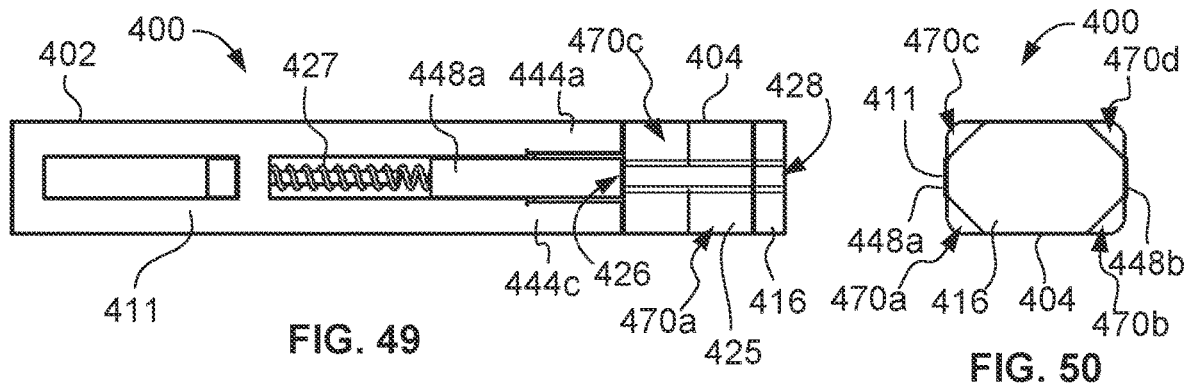
FIG. 49
FIG. 50

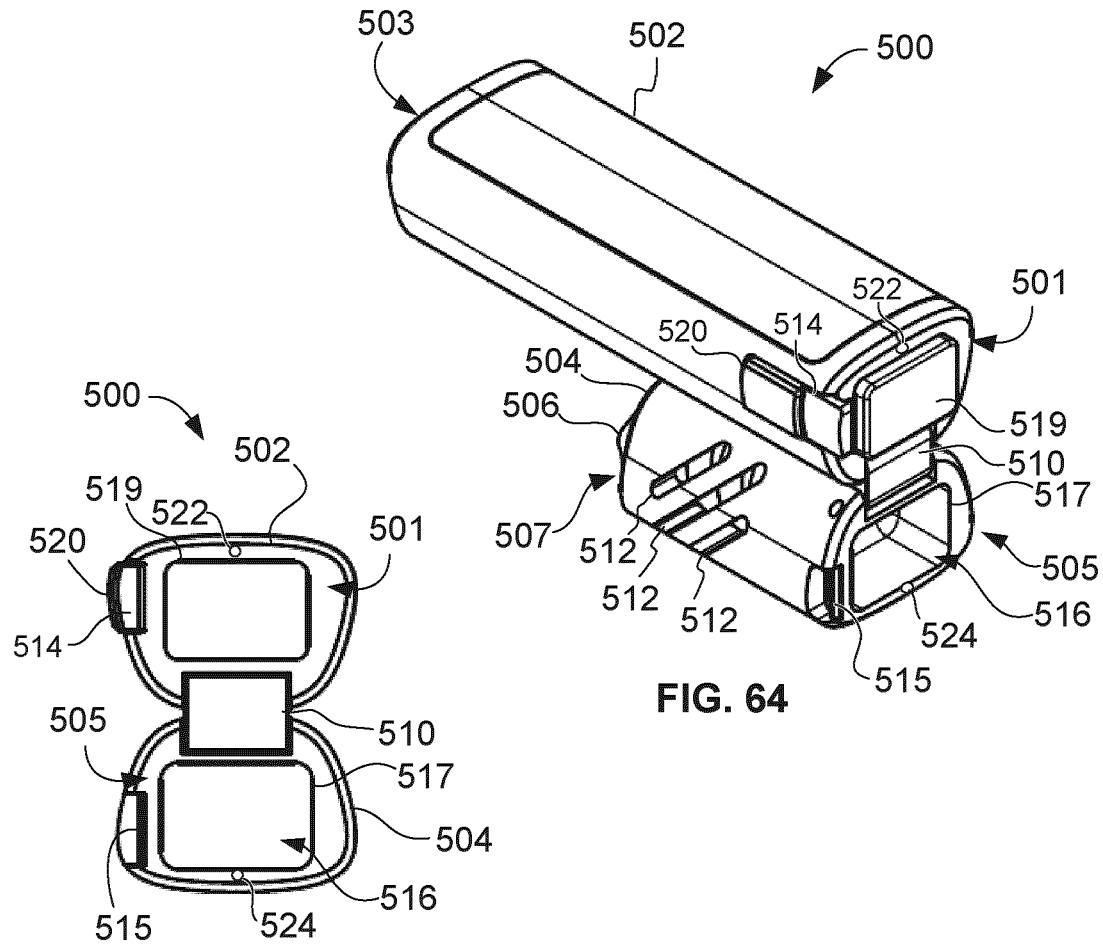
FIG. 64
FIG. 65
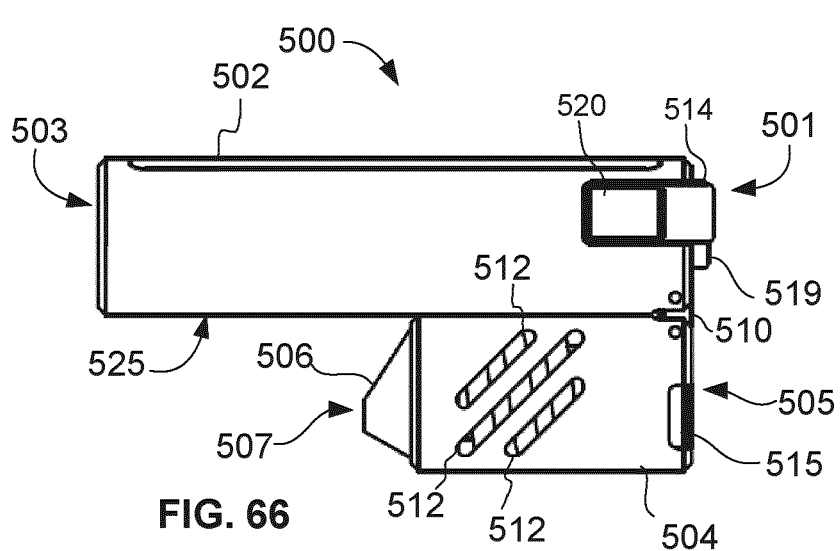
FIG. 66

VAPORIZER APPARATUSES HAVING A MOVABLE HEAD AND RELATED METHODS

RELATED APPLICATIONS

The present application is a 371 national-phase application of International Application No. PCT/CA2019/051093, filed Aug. 9, 2019, which in turn claims priority to U.S. Provisional Patent Application No. 62/717,479, filed Aug. 10, 2018, and to U.S. Provisional Patent Application No. 62/717,453, filed Aug. 10, 2018, the entire contents of all of which are incorporated herein by reference.

FIELD OF THE DISCLOSURE

The present disclosure relates generally to equipment used for vaporizing a material to emit a vapor for inhalation, and, more particularly to portable vaporizers for personal use.

BACKGROUND

Vaporizer apparatuses typically heat materials to create a vapor containing one or more desired extracted ingredients. Materials typically vaporized include dried plant material such as herbs, liquid-based compositions such as oils, wax-based compositions, etc. Such materials may be referred to as "vaporizing materials" herein. The vapor can then be delivered to a user by inhalation during a "vaping" session.

Portable vaporizer apparatuses for personal use are known. However, portable vaporizers for personal use may have functional limitations and can be bulky, thereby reducing the convenience of such vaporizers. As an example, existing portable vaporizer apparatuses typically have relatively simple activation mechanisms, such as an on/off button. These simple activation mechanisms are manipulated by a user to activate the vaporizer apparatus and create a vapor from the vaporizing material. However, these simple activation mechanisms can allow the vaporizer to be inadvertently activated at an undesired time (e.g. when the vaporizer is in a user's pocket). Additionally, simple activation mechanisms may allow an unsupervised child to activate the vaporizer apparatus, which can pose a danger to the child. Accordingly, the users of many typical portable vaporizers must be especially careful that the vaporizer apparatus is not inadvertently activated, either by themselves or by a child.

Portable vaporizer apparatuses for personal use are typically assembled from basic parts such as a mouthpiece, a vaporizing chamber for holding a material for vaporizing, a heating element, a battery, etc. Repeated use of these vaporizer apparatuses requires that a user must assemble and disassemble these various parts over and over again, which can result in parts being lost. In addition, the mouthpiece is typically not covered or otherwise protected between "vaping" sessions (i.e. when the vaporizer apparatus is not in use). This can be unhygienic for a user to position his or her mouth on the mouthpiece during a subsequent "vaping" session and can possibly lead to the unintentional inhalation of materials that may have fallen into the mouthpiece.

SUMMARY

In one aspect, there is provided a vaporizer apparatus comprising: a body; a head comprising a mouthpiece portion, the head being movable between an operational position and a non-operational position, and the head being engaged with the body in the operational and non-operational positions; a vaporizing chamber to receive a material and vaporizing means operatively coupled to the vaporizing chamber and operable to vaporize the material therein when activated, the vaporizing means being activatable when the head is in the operational position.

In some embodiments, the body has a docking portion and the head releasably engages the docking portion of the body in at least one of the operational position and the non-operational position.

In some embodiments, the body is elongate and has an end, wherein the docking portion is disposed in the end of the body.

In some embodiments, moving the head to the operational position enables activation of the vaporizing means, and moving the head out of the operational position disables the vaporizing means.

In some embodiments, in the operational position, the mouthpiece portion of the head is exposed and accessible.

In some embodiments, the head is removable from the body, and the docking portion comprises a docking bay that at least partially receives the head in the non-operational and operational positions.

In some embodiments, the non-operational position of the head is axially reversed relative to the operational position.

In some embodiments, the mouthpiece portion of the head is received in the docking bay in the non-operational position, and the mouthpiece portion of the head extends away from the docking bay in the operational position.

In some embodiments, the body comprises an outer housing and an inner body portion slidably received within the outer housing, and wherein the head abuts the inner body portion when received in the docking bay.

In some embodiments, the inner body portion is axially movable within the outer housing between a first longitudinal position and a second longitudinal position, the head being fully receivable into the docking bay in the first longitudinal position, and the head being partially ejected from the docking bay when the inner body portion is in the second longitudinal position.

In some embodiments, the vaporizer apparatus further comprises at least one of: a first at least one biasing element that biases the head to remain the operational position; a second at least one biasing element that biases the head to remain the non-operational position; and a third at least one biasing element that biases the inner body to remain in the first or second longitudinal position.

In some embodiments, the first and second at least one biasing element comprises at least one magnet.

In some embodiments, the third at least one biasing element comprises at least one spring.

In some embodiments, the head is collinear with the body in both the operational and non-operational positions.

In some embodiments, the head is movably attached to the body by a pivoting connection, and wherein pivoting the head generally about the pivoting connection moves the head between the non-operational position and the operational position.

In some embodiments, the pivoting connection comprises a hinge interconnecting the head and the body.

In some embodiments, the hinge comprises a double hinge.

In some embodiments, the head is collinear with the body in the operational position.

In some embodiments, the vaporizer apparatus further comprises at least one of: a first at least one biasing element that biases the head toward the operational position; and a second at least one biasing element that biases the head toward the non-operational position.

In some embodiments, the first biasing means comprises at least one first spring that urges the head to the operational position.

In some embodiments, the second biasing means comprises at least one second spring that urges the head to the non-operational position.

In some embodiments, at least one of the first and second at least one biasing element comprises one or more magnets.

In some embodiments, the vaporizing chamber is within the head, the body covering the vaporizing chamber when the head is in the operational position, and the vaporizing chamber being exposed when the head is in the non-operational position.

In some embodiments, the vaporizer apparatus further comprises a releasable latch that engages the head to secure the head in one of the operational position and the non-operational position.

In some embodiments, the body at least partially covers the mouthpiece portion of the head when the head is in the non-operational position.

In some embodiments, the head comprises a first one or more operative connectors, and the body comprises a second one or more operative connectors that engage the first one or more of the operative connectors to enable activation of the vaporizing means when the head is in the operational position.

In another aspect, there is provided a method for providing a vaporizer apparatus, comprising: providing a vaporizer apparatus head comprising a mouthpiece portion; and providing a vaporizer apparatus body comprising a docking portion that releasably engages the head in at least one of an operational position and a non-operational position.

In some embodiments, the docking portion at least partially receives the head in the operational position and the non-operational position, the head being removable from the docking portion.

In some embodiments, the method further comprises pivotably connecting the head and the body so that the head is movable between an operational position and a non-operational position, the head engaging the body in one of the operational position and a non-operational position.

Other aspects and features of the present disclosure will become apparent, to those ordinarily skilled in the art, upon review of the following description of the specific embodiments of the disclosure.

BRIEF DESCRIPTION OF THE DRAWINGS

The present disclosure will be better understood having regard to the drawings in which:

FIG. 12 is an upper perspective view of an inner body portion of the vaporizer apparatus of FIGS. 9 to 11 in isolation;

FIGS. 13 and 14 are upper perspective views of the vaporizer apparatus of FIGS. 9 to 11 with an outer housing removed to show the head seated on the inner body portion;

FIGS. 19 to 22 are upper perspective, lower perspective, side and front views, respectively, of the vaporizer apparatus of FIGS. 9 to 11 and 13 to 18 with the head docked in the front end of the body in the non-operational position;

FIGS. 23 to 26 are upper perspective, lower perspective, side and front views, respectively, of the vaporizer apparatus of FIGS. 9 to 11 and 13 to 22 with the head partially ejected from the body;

FIGS. 27 to 30 are upper perspective, lower perspective, side and front views, respectively, of another example vaporizer apparatus according to yet another embodiment with an outer housing removed and showing a head of the apparatus in an operational position;

FIGS. 31 to 34 are upper perspective, lower perspective, side and front views, respectively, of the vaporizer apparatus of FIGS. 27 to 30 with the outer housing removed and showing the head in a non-operational position;

FIGS. 47 to 50 of the vaporizer apparatus of FIGS. 43 to 46 according to still another embodiment with the outer housing removed and showing the head in a non-operational position;

FIGS. 64 to 66 are upper perspective, end, and side views, respectively, of the vaporizer apparatus of FIGS. 59 to 63 with the head pivoted to a non-operational position;

DETAILED DESCRIPTION

Aspects of the disclosure are not limited to the particular embodiments described herein. It is also to be understood that the terminology used herein is for the purpose of describing particular embodiments only and variations to the described embodiments may be made without departing from the scope of the claims.

As used herein the terms "a," "an," and "the" may include plural referents unless the context clearly dictates otherwise.

It is to be understood that directional or relative terms such as "forward", "front", "rearward", "back", "vertical", "horizontal", "side", "top", "bottom" and the like are used for ease of description and illustrative purposes, and embodiments are not limited to a particular orientation of the vaporizer apparatuses described herein during use or normal operation.

The present disclosure relates to vaporizers and related methods of vaporizing a material using a vaporizing apparatus. The term "vaporizer apparatus" may refer to any device configured to vaporize a material to produce a vapor to be inhaled by a user. The term "portable vaporizer apparatus" may refer to any vaporizer apparatus that is able to be carried by a user for portable use, such as vaporizer pens, portable dry herb vaporizers, electronic cigarettes, etc. Portable vaporizer apparatuses may be configured for use with one or more vaporizing materials including dried plant material such as herbs, liquid-based compositions such as oils, wax-based compositions, etc.

According to an aspect of the disclosure, a vaporizing apparatus comprises a body and a head which can be moved between two positions referred to herein as a "non-operational position" and an "operational position". The head may be engaged with the body in each of the "non-operational position" and the "operational position". The term "engaged with the body" in this context may refer to any engagement whereby the head is connected to, attached to, secured to or otherwise coupled to the body. For example, the head may abut or be partially received in the body. The head may be biased toward and/or releasably secured to the body. Any suitable mechanical or biasing coupling to hold the head in engagement with the body may be used.

Related methods for making a vaporizer apparatus are also provided. As used herein, the term "operational position" refers to the position of the head in which the vaporizer apparatus is ready or in condition to be used for "vaping" by a user. As used herein, the term "non-operational position" refers to a position of the head in which the vaporizer apparatus is not functional or ready for use.

FIGS. 1 to 8 illustrate an example vaporizer apparatus 100 according to an embodiment. The vaporizer apparatus 100 includes a body 102 and a head 104.

Figure 1:
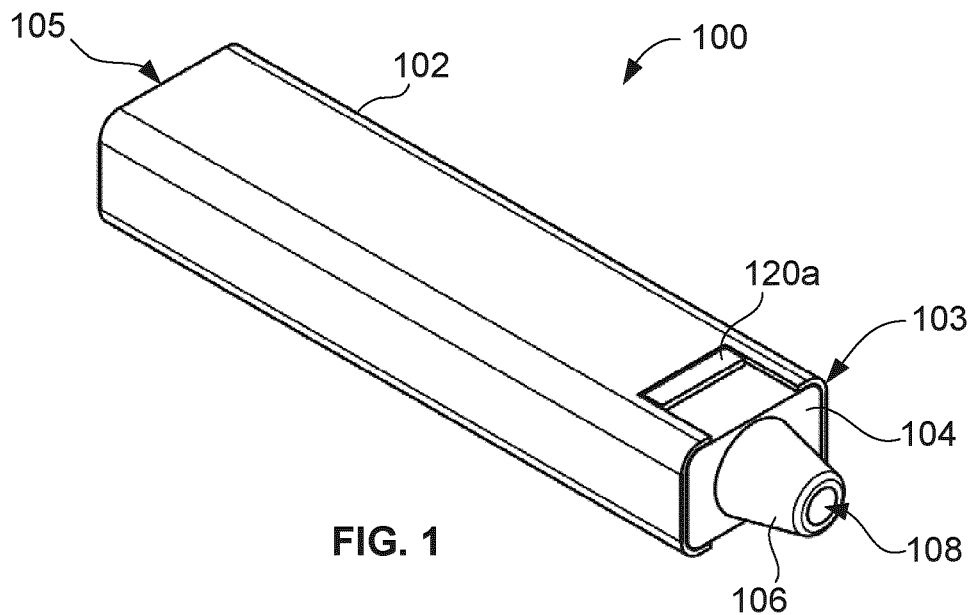
FIGS. 1 to 3 are upper perspective, side and end views, respectively, of an example vaporizer apparatus according to an embodiment with a head engaged with a body in an operational position.
Figure 2:
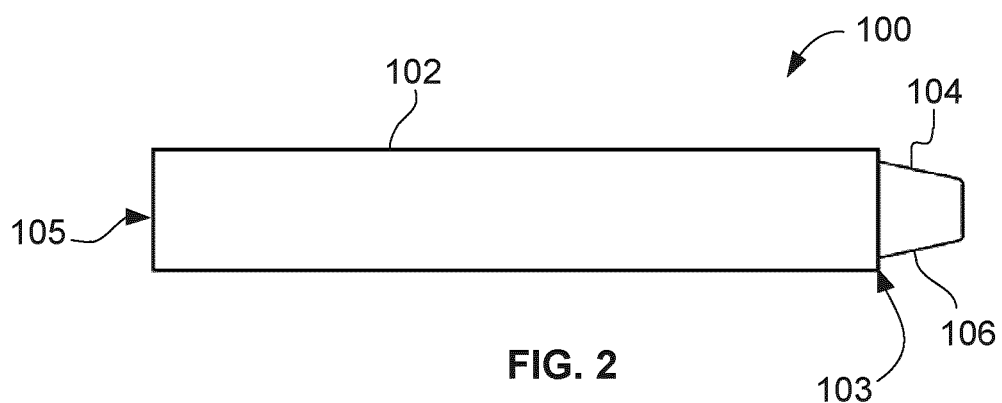
Figure 3:
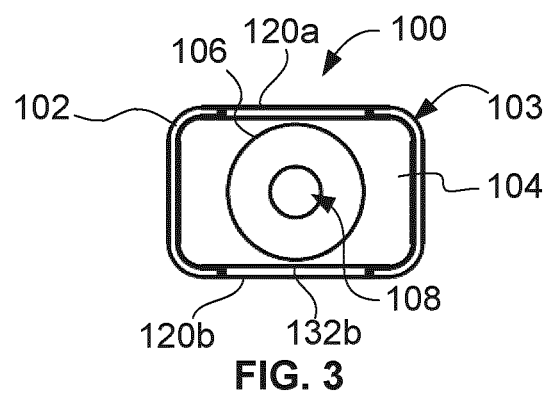
Figure 4:
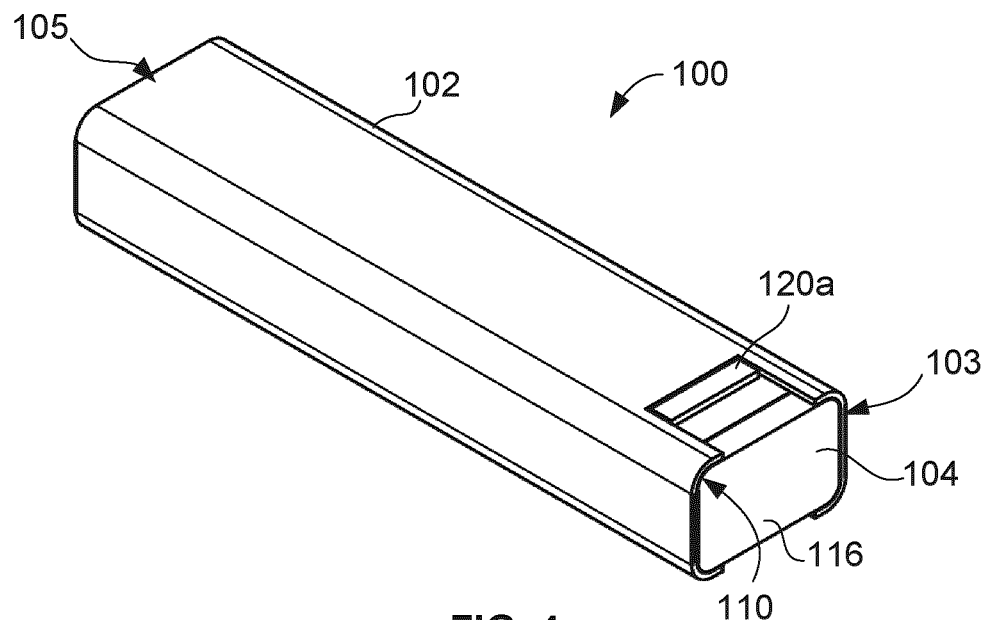
FIGS. 4 to 6 are upper perspective, side and end views, respectively, of the vaporizer apparatus of FIGS. 1 to 3 with the head in a non-operational position.
Figure 5:
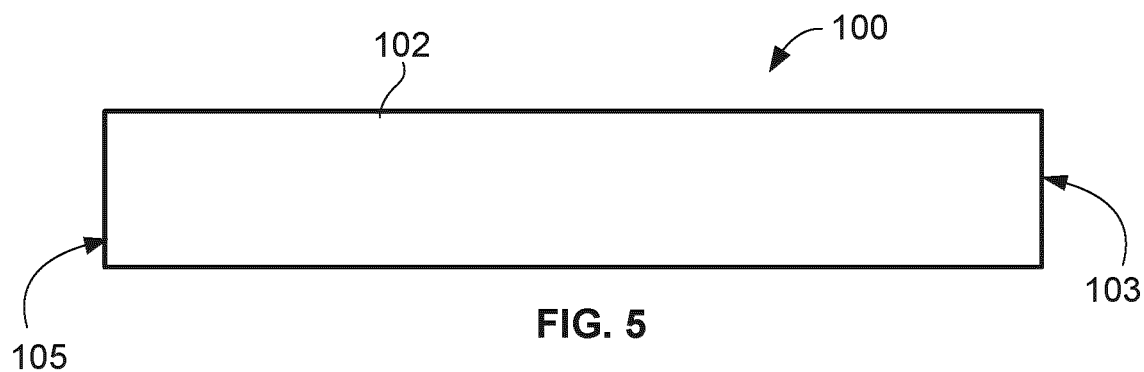
Figure 6:
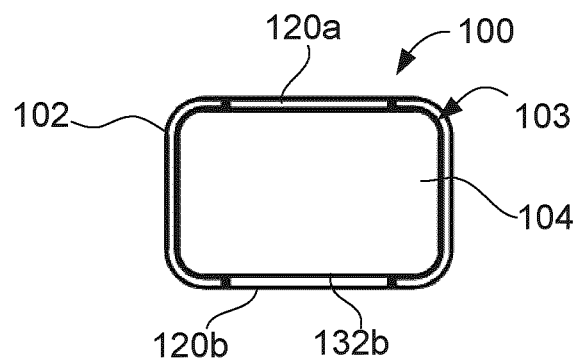

FIGS. 1 to 3 are upper perspective, side and end views, respectively, of the vaporizer apparatus 100 with the head 104 engaged with the body 102 in the operational position. FIGS. 4 to 6 are upper perspective, side and end views, respectively, of the vaporizer apparatus 100 showing the head 104 engaged with the body 102 in the "non-operational" position.

The body 102 in this embodiment is elongate having a first end 103 and an opposite second end 105. The head 104 releasably engages the first end 103 of the body. More specifically, in this example, the head 104 removably engages the first end 103 of the body 102 for both the "operational" and "non-operational" positions. More particularly, in this embodiment, the first end 103 is in the form of a docking bay 107 or seat for the head 104, and the head 104 docks with the first end 103. The head 104 is reversible such that the "operational" position of the head 104 is axially reversed relative to the "non-operational" position, where the term "axially" refers to a longitudinal axis of the vaporizer apparatus 100.

The head 104 in this embodiment comprises a mouthpiece portion 106 (shown in FIGS. 1 to 3). The head 104 further comprises a vaporizing chamber in fluid communication with the mouthpiece portion 106. The vaporizing chamber is not shown in FIGS. 1 to 8, but may be any chamber configured to hold a material for vaporizing. See, for example, the chamber 516 or 910 in FIGS. 64 and 90 respectively. The vaporizing chamber may hold a solid material such as a wax-based composition or dried plant material for vaporizing. In some embodiments, the vaporizing chamber may be a dry herb oven that can vaporize a portion of the plant material to emit a vapor. The vaporizing chamber may alternatively store and vaporize other solid materials, such as wax-based compositions. In other embodiments, the apparatus may comprise a reservoir to hold a liquid-based composition, and the chamber may receive the composition from the reservoir (e.g. via a wick).

The head 104 also comprises a vaporizing means operatively connected to the vaporizing chamber and activatable to vaporize the material in the vaporizing chamber. A vaporizing means may typically be a heating element that heats the chamber to vaporize the material, but embodiments are not limited to only heating-based vaporization. See, for example, heating element 912 in FIG. 90. The heating element may, for example, comprise a coiled heating element (e.g. metal coil filament), or any other element configured to generate sufficient heat to vaporize the vaporizing material. The heating element may, in some embodiments, only be activatable when the head 104 is in the operational position. When the head 104 is in the non-operational position, the vaporizer apparatus 100 is not operable for vaping. For example, the heating element may be disabled any time the head is not in the operational position.

Figure 7:
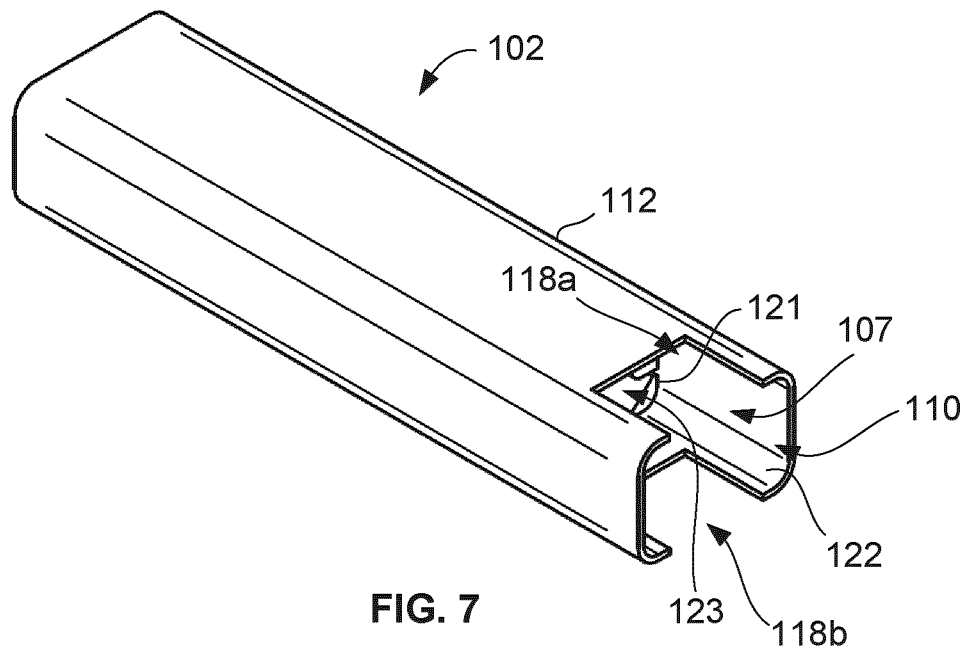
FIG. 7 is an upper perspective view of the body of the vaporizer apparatus of FIGS. 1 to 6 in isolation.

FIG. 7 is a perspective view of the body 102 of the vaporizer apparatus 100 of FIGS. 1 to 6 in isolation. The body 102 is generally elongate and rectangular or block-shaped in this embodiment, although embodiments are not limited to any particular shape of the body 102. For example, the body may be generally cylindrical, disc-shaped, or any other shape.

As shown, the body 102 comprises the docking bay 107 with an opening 110 at the first end 103 for receiving and docking the head 104 (not shown in FIG. 7) therein. The docking bay 107 is in the form of a recess in the first end 103 and is defined by a base 121 an outer wall 122 and at the first end 103. The base may be formed by an inner portion of the body 102, and the outer wall 122 may, for example, be formed by an outer housing 112 that covers the inner portion. The outer wall 122 includes opposing first and second recesses 118a and 118b or cutaways extending from the first end 103 and toward the second end 105. The body 102 may comprise one or more operative connection elements (e.g. electrical contacts, mechanical connectors, and/or air flow ports) within the docking bay 107 that engage corresponding operative connection elements in the head 104 when the head 104 is received in the operational position. Electrical contacts may be in the form of conductive strips or pads, male or female plug elements, or any other conductive contact point suitable for engaging another contact and forming an electrical connection. Thus, electrical power, control signals and/or airflow may be transferred from the body to the head or vice versa. The base 121 may define a further recess 123 or clearance space to receive and provide clearance for the mouthpiece portion 106 when the head 104 is in the non-operational positon.

Figure 8:
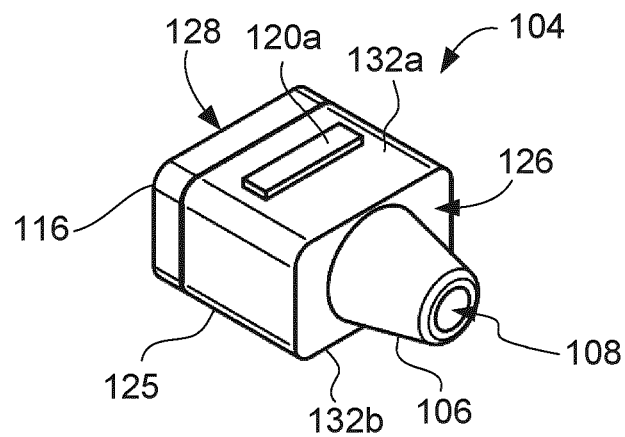
FIG. 8 is an upper perspective view of the head of the vaporizer apparatus of FIGS. 1 to 6 in isolation.

FIG. 8 is an upper perspective view of the head 104 of the vaporizer apparatus 100 of FIGS. 1 to 6 in isolation. As shown, the head 104 in this embodiment comprises a generally block-shaped core 125 that is shaped to fit within the docking bay 107 of the body 102 shown in FIG. 7. The core 125 has a first end 126 and an opposite second end 128.

The mouthpiece portion 106 extends from the first end 126 of the core 125. The mouthpiece portion 106 in this example defines a suction opening 108 therethrough. The vaporizing suction opening 108 may be in fluid communication with the vaporizing chamber in the core 125. The mouthpiece portion 106 in this example has a generally frustoconical shape, but embodiments are not limited to any particular mouthpiece shape.

The core 125 of the head 104, in this embodiment, comprises optional raised tabs 120a and 120b on top and bottom faces 132a and 132b (the tab 120b on the bottom face 132b is visible in FIGS. 3 and 6). The tabs 120a and 120b are shaped to be received in the first and second recesses 118a and 118b in the outer wall 122 of the docking bay 107 (shown in FIG. 7).

The head 104 may comprise one or more operative connection elements (e.g. electrical contacts, mechanical connectors, and/or air flow ports) that engage corresponding operative connection elements in the body 102. For example, such operative connection elements may be disposed on or near the second end 128 of the head 104. Thus, electrical power, control signals and/or airflow may be transferred between the body and the head. Such operative connection elements are not limited to any particular position in the docking bay 107 of the body 102 or the core 125 of the head 104.

Referring again to FIGS. 1 to 3, during a "vaping" session, a user can position head 104 in the "operational position" on vaporizer apparatus 100. To do so, the user may insert the core 125 of the head 104 into the docking bay 107, with the head 104 oriented such that the mouthpiece portion 106 is exposed and extends away from the body 102. The head 104 being in the operational position allows a user to fit his or her mouth on the mouthpiece portion 106 and inhale, which may cause vapor contained within the head 104 to be drawn through the suction opening 108 and into a user's mouth and lungs for consumption.

When the head 104 is in the operational position, in this embodiment, the vaporizer apparatus 100 is activatable to vaporize the material within the vaporizing chamber. For example, the body 102 may include a power source (e.g. battery), and the head 104 and body 102 may include cooperating electrical connectors (not shown) that engage each other only when the head 104 is received in the docking bay 107 in the operational position. The electrical connectors may carry power from the power source to the heating element to vaporize the material in the vaporizing chamber. Conversely, removing the head from the docking bay 107 would then disengage the electrical connectors such that the heating element cannot be activated.

FIGS. 4 to 6 show the vaporizer apparatus 100 with the head 104 in the non-operational position. In this embodiment, the head 104 may be coupled to the body 102 by inserting head 104 into the docking bay 107 via opening 110 (shown in FIG. 7) with the mouthpiece portion 106 extending into the body 102 (such that it is at least partially covered by the body and inaccessible). This position is axially reversed from the operational position. With head 104 in this position, the vaporizer apparatus 100 is not usable for vaping.

As shown, with head 104 in the non-operational position, the second end 128 of the core 125 may be pointed away from the body 102. The vaporizing chamber may be disposed near the second end 128 of the core 125, for example. The head 104 may further include a closure member 116 for providing access to the chamber. In some embodiments, the vaporizing chamber can be accessed by removing the closure member 116, thereby revealing the vaporizing chamber in head 104. The term "closure member" may refer to a cover, door, access panel, or any other removable or openable structure to provide access to the vaporizing chamber. In some embodiments, the vaporizing material can comprise a plant material.

To move the head 104 from the operational position to the non-operational position (and vice versa), the head 104 may be removed from the docking bay 107, flipped around axially by the user, and then placed back into the docking bay 107. To remove the head 104 from the first end 103 of the body 102, a user can slide tabs 120a and 120b of the head along the recesses 118a and 118b until the head 104 is more exposed and can be pulled away from out of the docking bay 107. However, as discussed further below, a person skilled in the art will realize that any number of mechanical arrangements could be used to allow removal the head 104 from the docking bay 107, and that recesses 118a and 118b and tabs 120a and 120b are only an example of one such a mechanical arrangement and is not a limitation of the disclosure.

Figure 59:
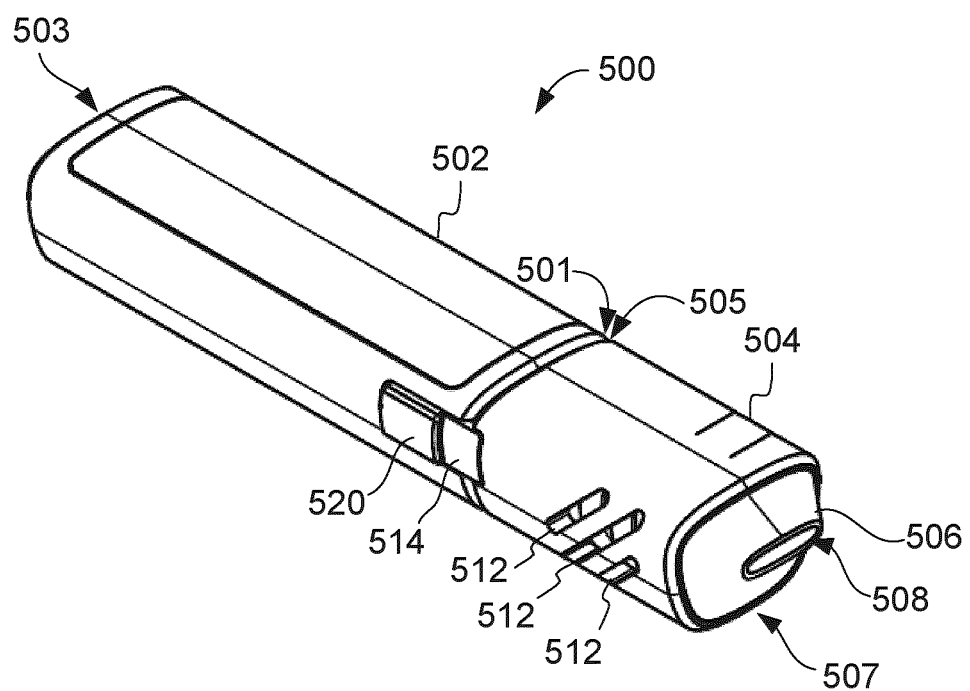
FIGS. 59 to 63 are upper perspective, bottom, side, top and front views, respectively, of an example vaporizer apparatus according to another embodiment with a pivoting head shown in an operational position.

The vaporizer apparatus 100 may further include one or more air intake openings in the head 104 and/or the body 102 that are in fluid communication with the vaporizing chamber and allow air intake into the chamber. The air may then pass from the chamber to the mouthpiece portion 106. Air intake openings are not shown in FIGS. 1 to 8 but may take any suitable form (see, for example, the air intake openings 512 of the vaporizer apparatus 500 in FIG. 59).

The vaporizing apparatus 100 may further comprise a power source such as a battery. The power source may be operatively connected to the heating element. The power source may be disposed in the body 102 or the head 104.

The vaporizer apparatus 100 may comprise one or more biasing elements to bias the head of the apparatus to remain engaged to the body in the operational position, the non-operational position, or both. The one or more biasing elements may include, without limitation, one or more magnets or physical snap fit components. In some embodiments, an attractive magnetic force can hold the head in the "operational position". For example, one or more magnets may be disposed in the body and positioned to be attracted to one or more corresponding ferrous metal elements in the head (or vice versa).

FIGS. 9 to 26 show an example vaporizer apparatus 200 according to another embodiment.

Figure 9:
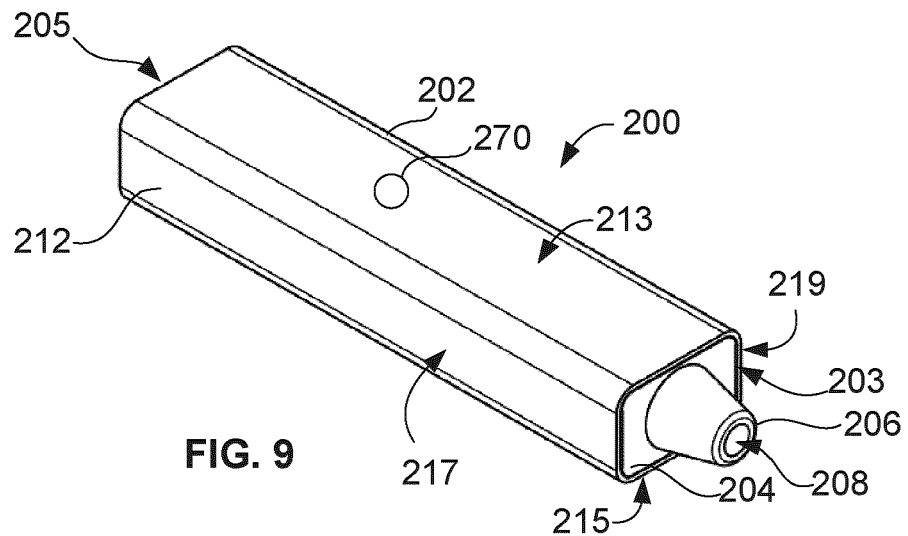
FIGS. 9 and 10 are upper and lower perspective views, respectively, of an example vaporizer apparatus according to another embodiment, with a head in an operational position.
Figure 10:
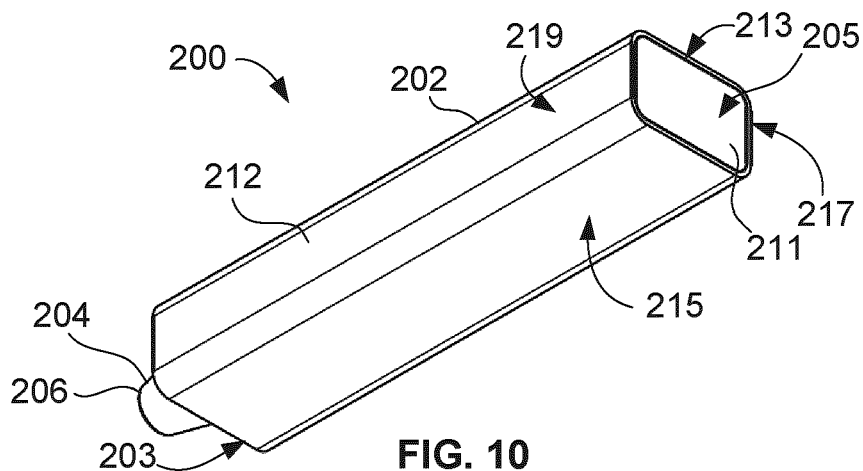

FIGS. 9 and 10 are upper and lower perspective views, respectively, of the vaporizer apparatus 200. As shown, the vaporizer apparatus 200 is shaped similarly to the embodiment shown in FIGS. 1 to 8 and comprises a body 202 and a head 204. The body 202 in this embodiment is elongate having a first end 203 and an opposite second end 205. The first end 203 may be referred to herein as a "front end" and the second end 205 may be referred to as a "back end" of the body 202 for ease of description. However, embodiments are not limited to a particular orientation of the vaporizer apparatus 200. The body 202 has a generally rectangular prism shape with a top 213, a bottom 215, a first side 217 and an opposite second side 219. However, as noted above, the head 204 and body 202 are not limited to any particular shape.

The head 204 releasably engages the front end 203 of the body and is reversible such that the operational position of the head 204 is axially reversed relative to the non-operational position. More specifically, in this example, front end 203 of the body is in the form of a docking bay 207 and the head 204 removably docks with the front end 203 of the body 202 for the operational and non-operational positions.

FIGS. 9 and 10 show the head 204 in the operational position. With the head 204 in this position, the vaporizer apparatus 200 is useable. The mouthpiece portion 206 and a suction opening 208 therein are exposed for use by a user in the operational position. Inhalation on the mouthpiece portion 206 may draw vapor formed in a vaporizing chamber within the head 204 through the suction opening 208.

In this embodiment, the body 202 comprises an inner body portion 211 and an outer housing 212 coupled to the inner body portion 211. The inner body portion 211 is axially movable relative to outer housing 212 between a forward position and a rearward position. The inner body portion 211 is shown in the rearward position in FIGS. 9 and 10. The outer housing 212 is tubular with open ends and extends longitudinally past the inner body portion 211 at the front end 203 of the body 202, thereby forming the docking bay 207. In this embodiment, the outer housing 212 is longer than the inner body portion 211 such that the inner body portion 211 is completely received in the outer housing 212, although embodiments are not limited to this arrangement.

Figure 11:
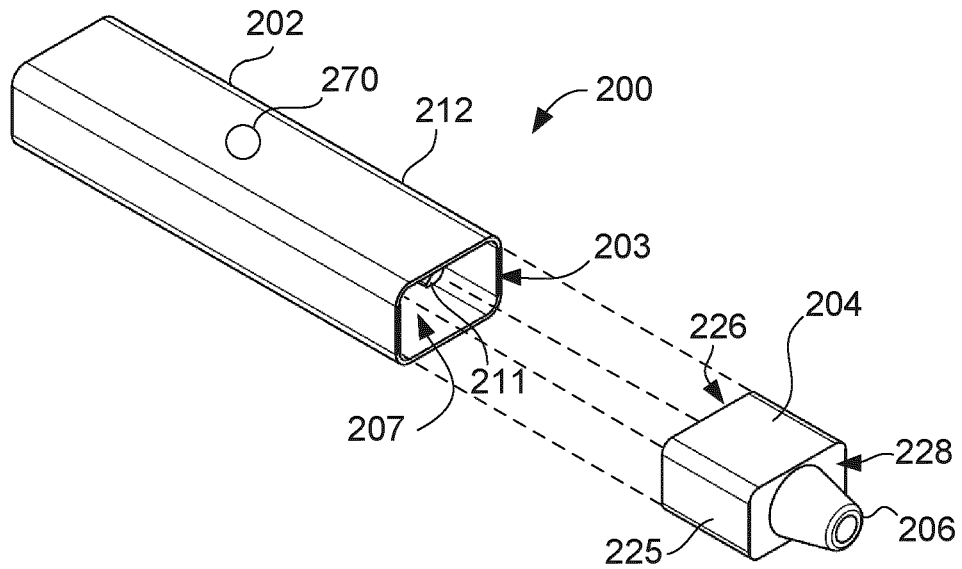
FIG. 11 is an exploded upper perspective view of the vaporizer apparatus of FIGS. 9 and 10.
Figure 15:
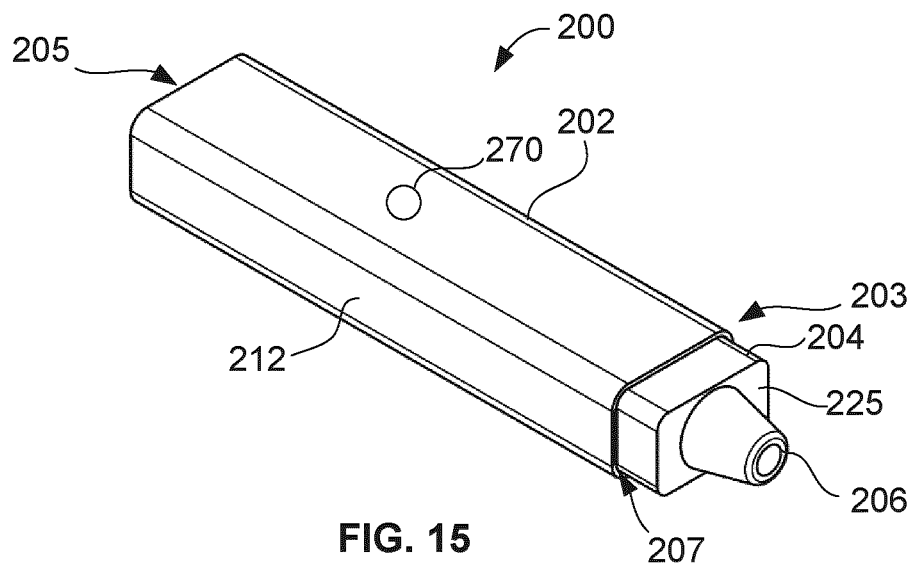
FIGS. 15 to 18 are upper perspective, lower perspective, side and front views, respectively, of the vaporizer apparatus of FIGS. 9 to 11, 13 and 14 with the head partially ejected from the body.
Figure 16:
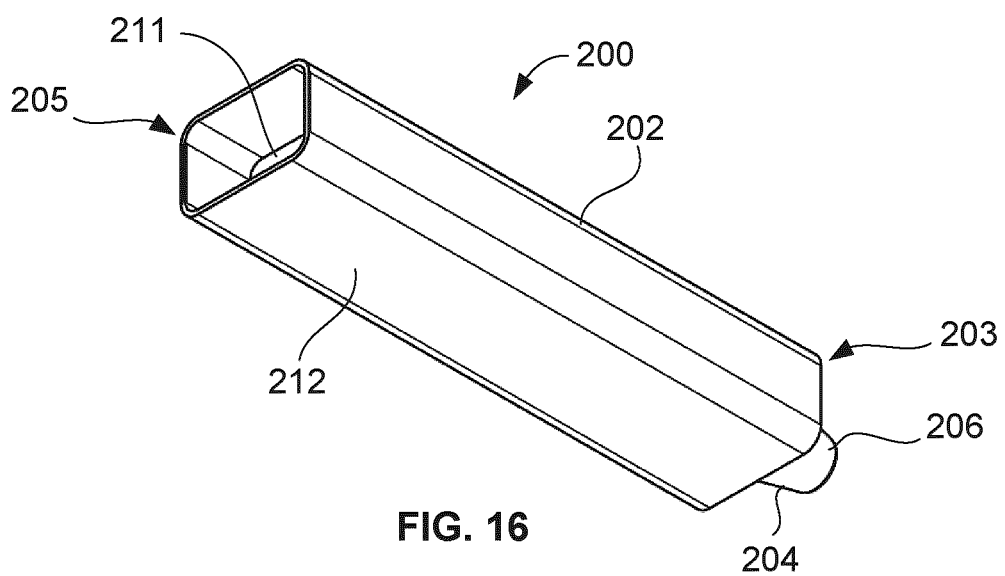
Figure 17:
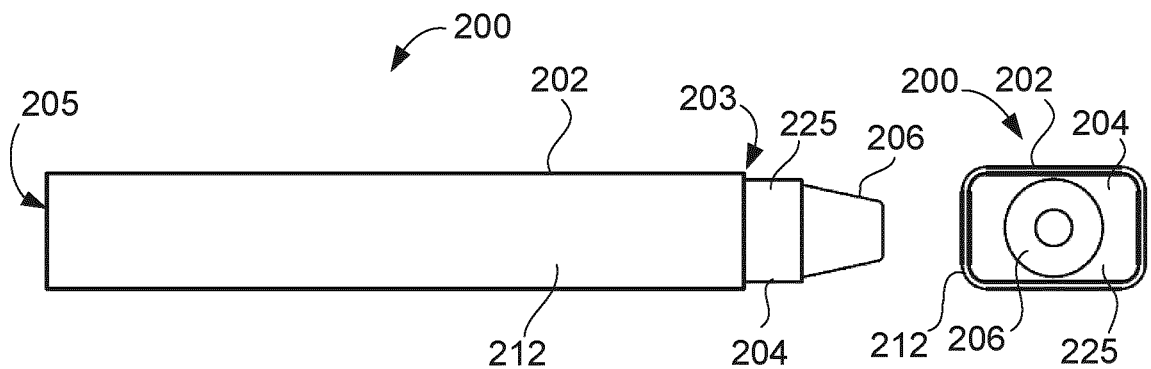
Figure 18:
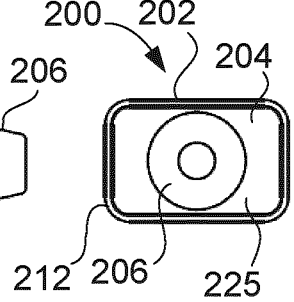

FIG. 11 is an exploded upper perspective view of the vaporizer apparatus 200. As shown, the head 204 in this embodiment comprises a generally block-shaped core 225 that is shaped to fit within the docking bay 207. The core 225 has a first end 226 and an opposite second end 228. The mouthpiece portion 206 extends from the first end 226. A vaporizing chamber (not shown) may be disposed within the head 204 near the second end 228, and the head 204 may include a removable or openable closure member (not shown) for accessing the vaporizing chamber. The core 225 is fully received in the front end 203 of the body in the operational and non-operational positions, although embodiments are not limited to this arrangement.

The docking bay 207 (shown in FIG. 11) is provided in the front end 203 of the body 202. The docking bay 207 receives the core 225 of the head 204 such that the head 204 seated on the inner body portion 211. The docking bay 207 has a first, full depth when the inner body portion 211 is in the rearward position and a second, partial depth when the inner body portion 211 is in the forward position. Thus, moving the inner body portion 211 to the forward position causes the head 204 to partially eject from the docking bay 207 to enable a user to more easily grip and remove the head 204. Thus, sliding movement of the inner body portion 211 may move the head 204 from a "fully docked" position to a "partially ejected" position.

With the head 204 removed as shown in FIG. 11, the head may be flipped axially to be reinserted into the docking bay 207 in the non-operational position (with the mouthpiece portion 206 covered). Access to the vaporizing chamber may allow materials for vaporizing to be positioned in the vaporizing chamber. In some embodiments, a closure member (not shown) of the head can be opened or removed to provide access to the vaporizing chamber. The closure member may be positioned on the core 225 and may be positioned away from the first end 226 of the core 225 so that the closure member is only accessible when vaporizer apparatus 200 is not in the operational position. For example, the closure member may be positioned at the second end 228 of the core 225.

FIG. 12 is an upper perspective view of the inner body portion 211 of the vaporizer apparatus 200 of FIGS. 9 to 11 in isolation. The inner body portion 211 comprises a frame member 230 that is slidingly received in the outer housing 212 (FIGS. 9 to 11). The frame member 230 has a front end 232 and a back end 234. The frame member also has top 236, bottom 238, first side 240 and second side 242, which are aligned with the top 213, bottom 215 and first and second sides 217 and 219 of the vaporizer apparatus 200 (FIGS. 9 and 10) when the inner body portion 211 is positioned in the outer housing 212. As shown, the frame member 230 in this embodiment has four prong extensions 244a to 244d extending from four corners of a front face 246 at its front end 232.

The frame member 230 moves relative to the outer housing 212. However, the inner body portion 211 in this embodiment also comprises components that are fixedly connected to the outer housing 212 and are movable relative to the frame member 230. In this example embodiment, the inner body portion 211 comprises rods 248a and 248b that are slidably received in respective channels 250 defined in the first and second sides 240 and 242 of the frame member 230. The rods 248a and 248b extend through the front face 246 of the frame member and extend toward the front end 232 of the inner body portion 211. The rods 248a and 248b in this example are fixed to an interior surface of the outer housing 212. Thus, the rods 248a and 248b and outer housing 212 move together relative to the frame member 230 of the inner body portion.

Optionally, the inner body portion 211 and the outer housing 212 further comprise a stopping mechanism to limit the sliding travel of the inner body portion 110. In this embodiment, the stopping mechanism comprises longitudinal slots 254 and tabs 256. Each of the first and second sides 240 and 242 of the inner body portion 211 defines one of the slots 254 therein (rearward of the channels 250 in this embodiment). Each tab 256 is received in a respective slot 254 and is fixed to the outer housing 212. In other embodiments, the tabs 256 may be integrated with the outer housing 212. The tabs 256 and slots 254 function as travel stops that limit the sliding, longitudinal movement of the inner body portion 211 relative to the outer housing 212. Any other suitable means to control or limit movement of the inner body portion 211 to the outer housing 212 may be used in other embodiments.

The vaporizer apparatus 200 may comprise one or more biasing or securing elements to hold the head 204 of the apparatus 200 engaged with the body 202 in the operational position, the non-operational position, or both. The one or more biasing elements may include, without limitation, one or more magnets, physical snap fit components, springs, or any other suitable means to bias or secure the head 204. For example, in some embodiments, a first one or more biasing elements may bias the head to remain in the "operational position". A second one or more biasing elements may bias the head to remain in the non-operational position. A third one or more biasing elements may bias the inner body portion 211 to remain in the rear and/or forward positions (i.e. making the rear and/or forward positions "neutral" positions so that force to overcome the bias is required to move away from the neutral positions).

In this embodiment, the first one or more biasing elements comprise magnets. Specifically, in FIG. 12, the inner body portion 211 includes first and second magnets 264a and 264b in ends 260a and 260b of the rods 248a and 248b. The head 204 may, for example, include ferrous metal pieces 266a and 266b (shown in FIG. 14) or additional magnets positioned on the second end 228 of the core 225. The ferrous metal pieces 266a and 266b are positioned to attractively engage the magnets 264a and 264b when the head is in the operational position (FIG. 13). In other embodiments, a securing means other than magnets or similar biasing force elements may secure the head in the operational and/or non-operational positions. Such securing means may include, but is not limited to, a detent mechanism, a latch, snap fit and/or friction fit configurations.

In this embodiment, the second one or more biasing elements comprises the same first and second magnets 264a and 264b in ends 260a and 260b of the rods 248a and 248b, as well as second ferrous metal pieces 268a and 268b (shown in FIG. 13) positioned on the first end 226 of the core 225 of the head 204. The second ferrous metal pieces 268a and 268b are positioned to attractively engage the magnets 264a and 264b of the inner body portion 211 when the head is in the non-operational position (FIG. 14). Embodiments are not limited to any number, type, or positioning of biasing elements to bias the head 204 to remain engaged with the body 202 in the operational position and/or the non-operational position. Such biasing elements may also be omitted in other embodiments.

In this embodiment, the third one or more biasing means includes springs 227 that bias the inner body portion 211 to remain in the rearward position. Referring to FIG. 12, the inner body portion 211 comprises two springs 227, each between a respective one of the rods 248a and 248b and corresponding rearward end 252 of the channels 250. The springs 227 bias the rods 248a and 248b toward the front end 232 of the frame member 230, thereby biasing the frame member 230 to remain in the rearward position relative to the outer housing 212 (FIGS. 9 to 11). Thus, the rearward position of the inner body portion 211 is a "neutral" position in this embodiment, meaning that the inner body portion 211 may remain in the rearward position absent force applied by a user or other source to overcome the force of the springs. One or more other biasing elements (e.g. magnets) may also be used to hold the inner body portion 211 in the forward position. Such elements may be used in combination with the springs 227.

In other embodiments, the springs 277, rods 248a and 248b, and the channels 250 may be omitted. The inner body portion may simply slide between rearward and forward positions without being biased by such springs. In such embodiments, one or more stopping mechanisms may be included to limit the travel of the inner body portion, and one or more different biasing means (e.g. magnets) or securing mechanisms may be used to bias or hold the inner body portion in one or more neutral or stable positions. As another option, a detent or catch mechanism may be used to secure the inner body portion in one or more positions. For example, a detent mechanism may comprise a raised protrusion (e.g. bump) on an outer surface of the inner body portion and a depression on the inner surface of the outer housing (or vice versa). The protrusion may be biased in an extended position. For example, the protrusion may be spring loaded to allow the protrusion to be pushed inward, or the protrusion may comprise a deformable material. The protrusion may be compressed to overcome the bias, allowing the protrusion to move out of the depression, thereby allowing the inner body portion to move relative to the outer housing. Another example of a detent mechanism is a diving board style protrusion having a bump on its end (receivable in the depression).

When the inner body portion 211 is in the rearward position, in this example embodiment, ends 258a to 258d of the prong extensions 244a to 244d are approximately level with ends 260a and 260b of the rods 248a and 248b. The core 225 of the head 204 may, thus, abut each of the ends 258a to 258d and 260a and 260b when docked with on the body 202 in the operational and non-operational positions.

When the head 204 is in the operational position one or more electrical contacts in the head may engage one or more electrical contacts in the body 202. In this example, electrical contacts 262a to 262d are disposed in the ends 258a to 258d of the prong extensions 244a to 244d for engaging one or more corresponding electrical contacts in the head. Such contacts may carry power and/or control signals from the body 202 to the head 204.

If a user moves the frame member 230 in the forward direction (indicated by arrow "A" in FIG. 12) relative to the outer housing 212, the frame member 230 also moves relative to the rods 248a and 248b and tabs 256. Thus, rods 248a and 248b move in the rearward direction (indicated by arrow "B" in FIG. 12) relative to the remainder of the inner body portion 211, compressing the spring 227.

A skilled person in the art would realize that the first, second, and third one or more biasing elements are not limited to magnets or springs, and a number of different biasing mechanisms could be employed in the vaporizer apparatus 200. Magnetic forces and spring forces are only provided as example embodiments the first or second biasing elements. Further, combinations of biasing elements could also be utilized to achieve desired biasing characteristics to bias the head 204 in either the operational position or the non-operational position. In still other embodiments, rather than biasing elements such as magnets or springs, mechanical securing means (hooks, snap fit elements, friction fit elements, etc.) may be used to releasably secure the head in position and/or to hold the inner body portion in the forward and/or rearward position. Embodiments are not limited to a particular manner of providing stable and/or neutral positions and configurations of the vaporizer apparatuses described herein.

FIGS. 13 and 14 are upper perspective views of the vaporizer apparatus 200 with the outer housing 212 removed to show the head 204 seated on the inner body portion 211. FIG. 13 shows the example head 204 oriented for the operational position. The second end 228 of the head 204 abuts the inner body portion 211, and the mouthpiece portion 206 extends forward, away from the inner body portion 211. Specifically, in this example embodiment, second first end 228 of the core 225 abuts the prong extensions 244a to 244d and the rods 248a and 248b.

FIG. 14 shows the head 204 oriented for the non-operational position. The first end 226 of the core 225 of the head 204 abuts the prongs inner body portion 211. Specifically, the first end 226 of the core 225 abuts the prong extensions 244a to 244d and the rods 248a and 248b and the mouthpiece portion 206 extends rearward into the space between the prong extensions 244a to 244d and the rods 248a and 248b.

FIGS. 15 to 18 are upper perspective, lower perspective, side and front views, respectively, of the vaporizer apparatus 200 with the inner body portion 211 of the body 202 moved to the forward position relative to the outer housing 212. From the operational position shown in FIG. 9, a user may push forward on the inner body portion 211 at the back end 205 of the body 202. This pushing moves the inner body portion 211 forward relative to the outer housing 212. The head 204 partially ejects from the docking bay 207 (shown in FIG. 11) at the front end 203 of the body. In this embodiment, the core 225 of the head is fully received in the docking bay 207 when the inner body portion 211 is in the rearward position, and the core 225 partially extends out of the docking bay 207 when the inner body portion 211 is pushed forward. The user may then grip and remove the head 204. With the head 204 removed, the user may flip the head axially and reinsert the head into the docking bay 207 in the non-operational position (with the mouthpiece pointing into the body 202).

FIGS. 19 to 22 are upper perspective, lower perspective, side and front views, respectively, of the vaporizer apparatus 200 with the head 204 docked in the front end 203 of the body 202 in the non-operational position. The inner body portion 211 is in the rearward position, with the core 225 flush with the end 203 of the body 202. As shown, the mouthpiece 206, which was exposed in the operational position, is now positioned within the front end 203 of the body 202 and is covered and not accessible. With the head 204 in this position, the vaporizer apparatus 200 is not useable and may be relatively convenient to store or transport between "vaping" sessions. Partial or complete coverage of mouthpiece portion 206 may also provide some protection to the mouthpiece portion 206 when vaporizer apparatus 200 is not being used, potentially making vaporizer apparatus 200 more hygienic. Unwanted material may be blocked from entering mouthpiece portion 206.

As shown in FIGS. 10 and 19, in this embodiment, when the inner body portion 211 is in the rearward position, the inner body portion 211 is flush with the back end 205 of the body 202 and outer housing 212. Embodiments are not limited to this particular arrangement, and, in other embodiments, the inner body portion 211 may extend from the outer housing 212 or be recessed relative to the outer housing 212 in the rearward position.

FIGS. 23 to 26 are upper perspective, lower perspective, side and front views, respectively, of the vaporizer apparatus 200 with the inner body portion 211 pushed forward relative to the outer housing 212 of the body 202. From the non-operational position shown in FIGS. 19 to 22, a user may push forward on the inner body portion 211 at the back end 205 of the body 202 so that is moves forward relative to the outer housing 212. This causes the head 204 to partially protrude from the front end 203 of the body 202 so that a user can grip and remove the head 204.

In some embodiments, the vaporizer apparatus 200 may include one or more user controls. The one or more user controls may activate the vaporizer apparatus 200 when the head 204 is in the operational position. The one or more user controls may comprise a button. An example button 270 is shown in FIGS. 9, 11 to 15, 19 and 23. The button 270 can be pressed to activate the heating element in the head 204 in order to generate a vapor from the vaporization materials. The button 270 may be integrated with the inner body portion 211 and extend through the outer housing 212, by way of example. Embodiments are not limited to the inclusion of buttons. Any activation mechanism could be employed to activate the heating element and pressing a button to activate the heating element is not a limitation to the disclosure. For example, the heating element may be activated automatically by a sensor detecting that a user is inhaling through the mouthpiece portion.

Additionally, in some embodiments, heating element may only be activatable when the head 204 is in the operational position. In other words, the vaporizer apparatus 200 may, in some embodiments, not be turned on when head 204 is not in the operational position, thereby decreasing the possibility of inadvertent activation. In some embodiments, the operative connection between the button (or other user interface element) and the heating element is formed only when head is in the operational position. In some embodiments, the vaporizer apparatus 200 may include a sensor (not shown) mounted on the head 204 that senses the position of the head 204 with respect to the body 202. The sensor may provide output, and the heater may only be enabled when output from the sensor indicates that the head 204 is in the operational position. As also noted above, electrical connections may be made between the head 204 and the body 202 when the head 204 is in the operational position. Thus, moving the head away from the operational position may break such connections, thereby disabling the heating element in the head.

In some embodiments, the vaporizer apparatus 200 is only activatable by pressing the button 270 if the head 204 is engaged with the body 202 in the operational position. Therefore, in some embodiments, a user may be relatively confident that the vaporizer apparatus 200 is not going to be activated when the head 204 is in the non-operational position. This may decrease the possibility that the vaporizer apparatus 200 will be either inadvertently activated, or activated by a child. In some embodiments, activation of vaporizer apparatus 200 can be achieved by simultaneously pressing the button 270 and positioning head 204 to the operational position.

The vaporizer apparatus 200 may further include one or more air intake openings (not shown) in the head 204 and/or the body 202 that are in fluid communication with the vaporizing chamber and allow air intake into the chamber. The air may then pass from the chamber to the mouthpiece.

FIGS. 27 to 42 illustrate an example vaporizer apparatus 300 according to yet another embodiment. The vaporizer apparatus 300 includes a body 302 and a head 304 that engages the body 302. In FIGS. 27 to 34, an outer housing 312 (shown in FIGS. 35 to 42) of the body 302 is removed to show the inner body portion 311 engaged with the head 304. The vaporizer apparatus 300 includes is similar in structure and function to the vaporizer apparatus 200 shown in FIGS. 9 to 26, with some differences discussed below.

FIGS. 27 to 30 are upper perspective, lower perspective, side and front views, respectively, of the vaporizer apparatus 300 showing the head 304 engaged with the inner body portion 311 in the operational position.

FIGS. 31 to 34 are upper perspective, lower perspective, side and front views, respectively, of the vaporizer apparatus 300 showing the head 304 showing the head 304 engaged with the inner body portion 311 in the non-operational position.

The inner body portion 311 in the embodiment shown in FIGS. 27 to 34 has shorter side channels 354 with tabs 356 received therein for limiting the sliding movement of the inner body portion 311. Thus, the allowable axial travel of the inner body portion 311 relative to the outer housing 312 (shown in FIGS. 35 to 42) is shorter than in the embodiment of FIGS. 9 to 26.

In addition, the head 304 in FIGS. 27 to 34 is shown with a removable chamber closure member 316 at the end 328 opposite to the mouthpiece portion 306. The chamber closure member 316 may be removed to provide access to the vaporizing chamber within the head 304.

Similar to the embodiment in FIGS. 9 to 26, the inner body portion 311 of the vaporizer apparatus 300 in FIGS. 27 to 42 is slidable relative to the outer housing 312 to move between rearward and forward positions. In the forward position, the inner body portion pushes the head 304 to partially extend from the front end 303 of the body 302.

Figure 35:
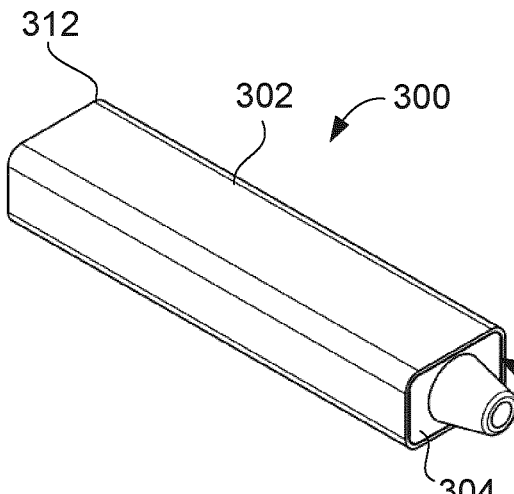
FIGS. 35 and 36 are upper perspective and lower perspective views, respectively, of the vaporizer apparatus of FIGS. 27 to 34 with the head engaged with a body in the operational position.
Figure 36:
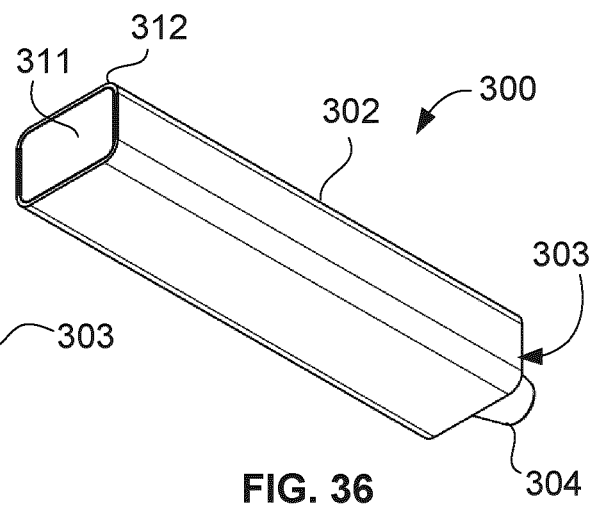

FIGS. 35 to 42 show the vaporizer apparatus 300 including the outer housing 312. FIGS. 35 and 36 are upper perspective and lower perspective views, respectively, of the vaporizer apparatus 300 with the inner body portion 311 in the rearward (neutral) position relative to the outer housing 312 and the head 204 engaged with the body 302 in the operational position.

Figure 37:
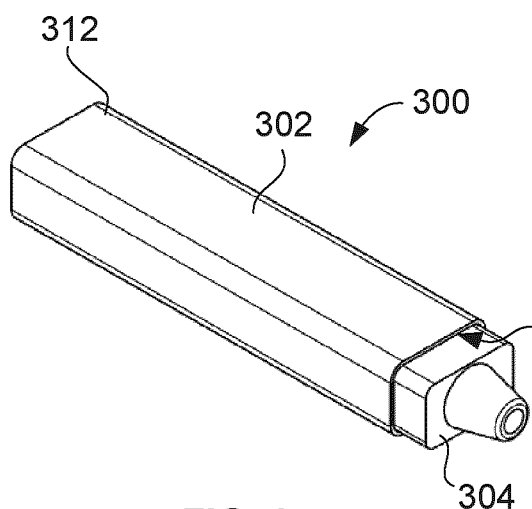
FIGS. 37 and 38 are upper perspective and lower perspective views, respectively, of the vaporizer apparatus of FIGS. 35 and 36 with the head partially ejected from the body.
Figure 38:
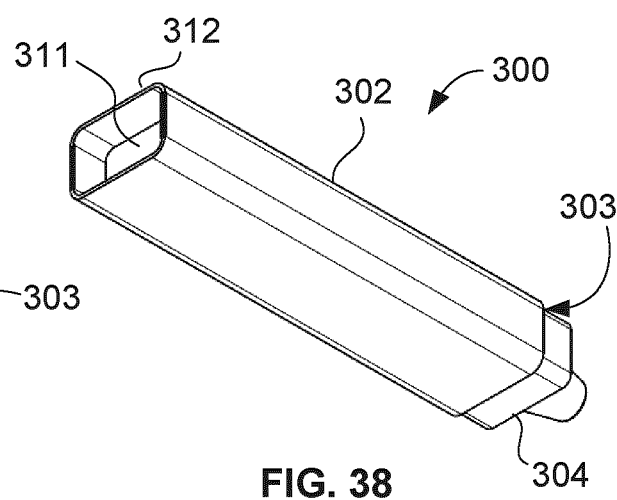

FIGS. 37 and 38 are upper perspective and lower perspective views, respectively, of the vaporizer apparatus 300 with the head 304 still oriented in the same direction as in FIGS. 35 and 36, but with the inner body portion 311 pushed to the forward position so that the head is partially ejected from the body 302 (i.e. extends further from the body 302 than in FIGS. 35 and 36).

Figures 39, 40:
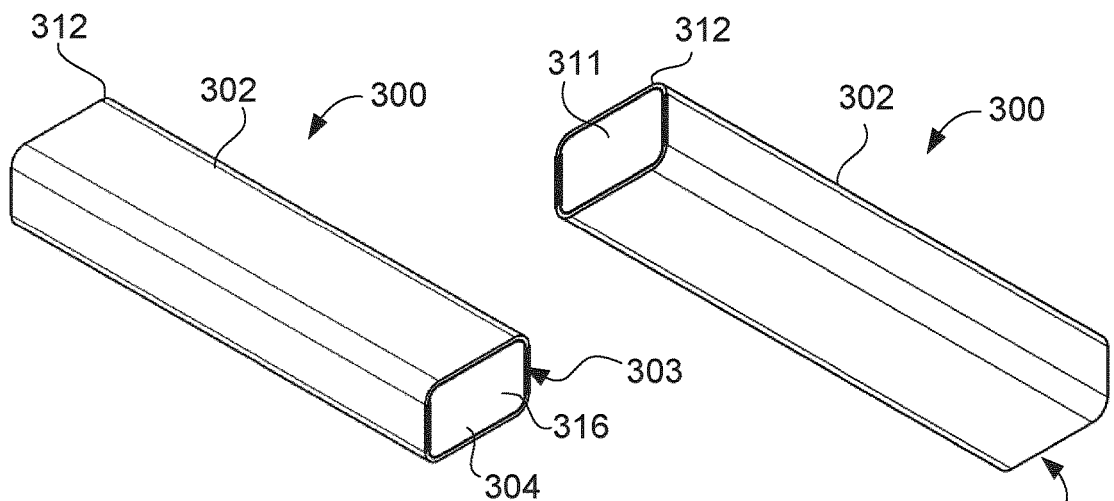
FIGS. 39 and 40 are upper perspective and lower perspective views, respectively, of the vaporizer apparatus of FIGS. 27 to 34 with the head engaged with the body in the non-operational position.

FIGS. 39 and 40 are upper perspective and lower perspective views, respectively, of the vaporizer apparatus 300 with the inner body portion 311 in the rearward (neutral) position relative to the outer housing 312 and the head 204 engaged with the body 302 in the non-operational position.

Figures 41, 42:
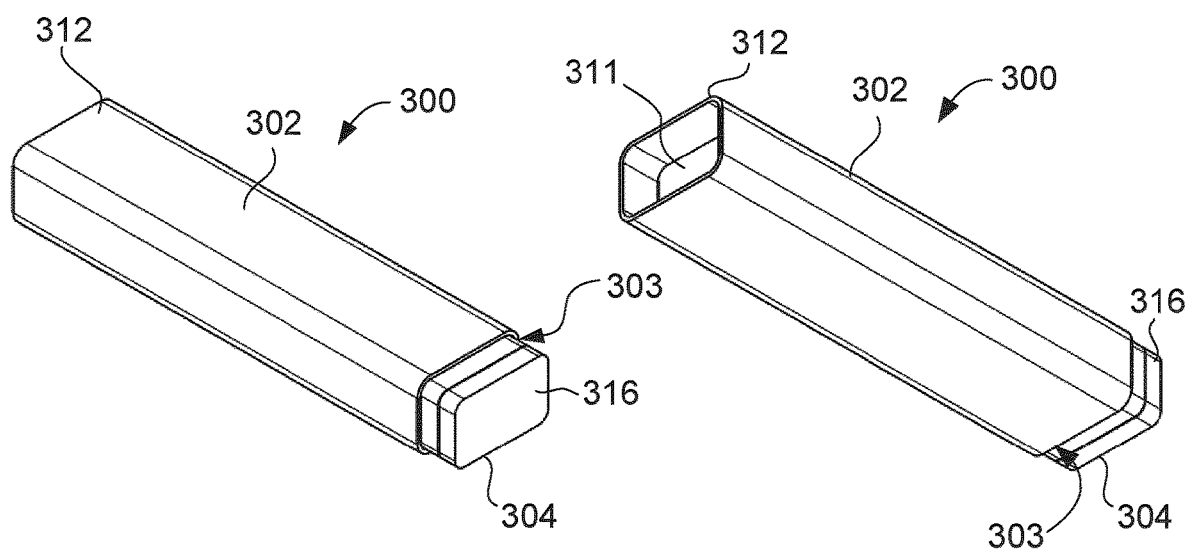
FIGS. 41 and 42 are upper perspective and lower perspective views, respectively, of the vaporizer apparatus of FIGS. 39 and 40 with the head partially ejected from the body.

FIGS. 41 and 42 are upper perspective and lower perspective views, respectively, of the vaporizer apparatus 300 with the inner body portion 311 pushed forward relative to the outer housing 312, with the head 304 oriented with the mouthpiece portion 306 (FIGS. 27 to 30) pointing into the body 302. As shown, the head 304 extends from the body 302 such that the chamber closure member 316 may be removed in this position without totally removing the head 304.

One or more operative connection elements (e.g. electrical contacts, mechanical connectors, and/or air flow ports) may be provided on the head 304 to engage corresponding operative connection elements in the body, similar to other embodiments described herein.

According to some embodiments, the vaporizer apparatus 300 may include one or more child-safety lock mechanisms to decrease the likelihood of a child using the vaporizer apparatus 300 and/or opening the vaporization chamber in the head 304 and accessing the materials contained therein. In some embodiments, access to the vaporizing chamber can require moving the inner body portion 311 to the forward position relative to the outer housing 312 (so that the head 304 partially ejects) and grasping the head 304 and removing the head 304 from the vaporizer apparatus 300, and removing the closure member 316 to reveal the vaporizing chamber. As used herein, the term "child-lock safety device" can refer to any device that is designed to help prevent a child or an unauthorized user from performing any action that poses a danger to the child or the unauthorized user. When used in reference to vaporizer apparatus 300, a "child-lock safety device" can refer to any device that is designed to help prevent a child or an unauthorized user perform any action with vaporizer apparatus 300 that would pose a danger to the child or unauthorized user, for example, access the materials to be vaporized or activate the heating element. As used herein, the term "unauthorized user" can refer to any person that does not have authorization to use vaporizer apparatus 300, including, for example, persons having diminished mental capacity because of illness or disability such as a mental health problem, dementia, or learning disability.

The vaporizer apparatus 300 may further include one or more air intake openings (not shown) in the head 304 and/or the body 302 that are in fluid communication with the vaporizing chamber and allow air intake into the chamber. The air may then pass from the chamber to the mouthpiece.

FIGS. 43 to 50 illustrate an example vaporizer apparatus 400 according to still another embodiment. The vaporizer apparatus 400 includes a body 402 and a head 404 that engages the body 402. In FIGS. 43 to 50, an outer housing 412 (shown in FIGS. 51 to 58) of the body 402 is removed to show the inner body portion 411 engaged with the head 404. The vaporizer apparatus 400 is similar in structure and function to the vaporizer apparatuses 200 and 300 shown in FIGS. 9 to 42, with some differences discussed below.

FIGS. 43 to 46 are upper perspective, lower perspective, side and front views, respectively, of the vaporizer apparatus 400 showing the head 404 engaged with the inner body portion 411 in the operational position.

FIGS. 47 to 50 are upper perspective, lower perspective, side and front views, respectively, of the vaporizer apparatus 400 showing the head 404 engaged with the inner body portion 411 in the non-operational position.

In this embodiment, the core 425 and closure member 416 of the head 404 is sized and configured to at least partially fit or "nest" within the inner body portion 411 when the head 404 is in the operational position. The "nesting" of the core 425 and closure member 416 may provide for more surface contact between the inner body portion 411 and the head 404, thereby providing more options for operative connections (e.g. electrical connections) between components of the head 404 (e.g. heating element) and the body 402 (e.g. power source). This "nesting" may also provide some physical protection for the nested portion of the core 425. In this embodiment, the nesting functionality is provided by four corner cut-outs or recesses 470a to 470d (best shown in FIGS. 47 to 50) in the core 425, which extend from the second end 428 of the core and part way toward the first end 426. The corner recesses 470a to 470d (beveled corners in this embodiment) are shaped and positioned complimentary to the prongs 444a to 444d of the inner body portion 411. The prongs 444a to 444d are receivable in the recesses 470a to 470d for the core 425 of the head 404 to nest within the prongs 444a to 444d when the head is mounted in the operational position shown in FIGS. 43 to 46.

With the head 404 nested in the inner body portion 411 as shown in FIGS. 43 to 46, the rods 448a and 448b are partially moved rearward, thereby partially compressing the springs 427. The vaporizer apparatus 400 may include a biasing or releasable securing element or mechanism to hold the head 404 in this nested position so that the force from the springs 427 (or other forward biasing element of the inner body portion) does not eject the head 404 during normal operation. For example, the vaporizer apparatus 400 may include one or more magnets and/or ferrous metal pieces similar to magnets 264a and 264b and metal pieces 266a and 266b shown in FIGS. 12 to 13. Any other suitable releasable securing means may also be used (e.g. snap fit or friction fit components). From the nested position, a user may push the inner body portion 411 further forward relative to the outer housing 412 to overcome the releasable securing means and partially eject the head 404 for removal similar to other embodiments described herein.

Similar to the embodiment in FIGS. 9 to 20, the inner body portion 411 of the vaporizer apparatus 400 in FIGS. 27 to 44 is slidable relative to the outer housing 412 to move between rearward and forward positions. In the forward position, the inner body portion pushes the head 404 to partially extend from the front end 403 of the body 402.

FIGS. 51 to 58 show the vaporizer apparatus 400 including the outer housing 412.

Figure 51:
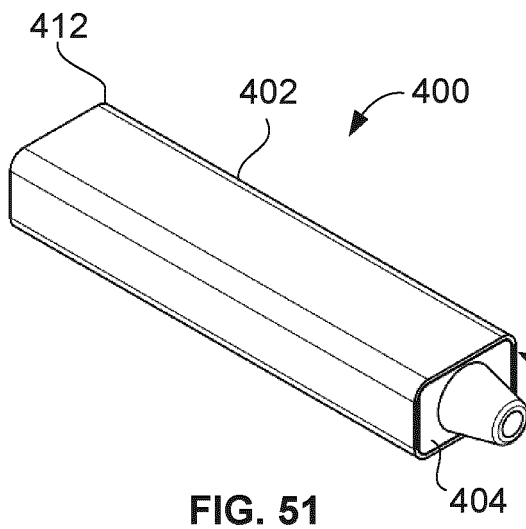
FIGS. 51 and 52 are upper perspective and lower perspective views, respectively, of the vaporizer apparatus of FIGS. 43 to 50 with the head engaged with a body in the operational position.
Figure 52:
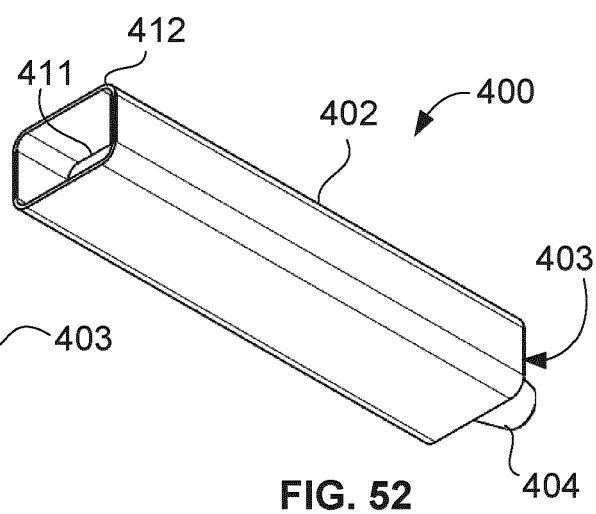

FIGS. 51 and 52 are upper perspective and lower perspective views, respectively, of the vaporizer apparatus 400 with the inner body portion 411 in the rearward (neutral) position relative to the outer housing 412 and the head 204 engaged with the body 402 in the operational position.

Figure 43:
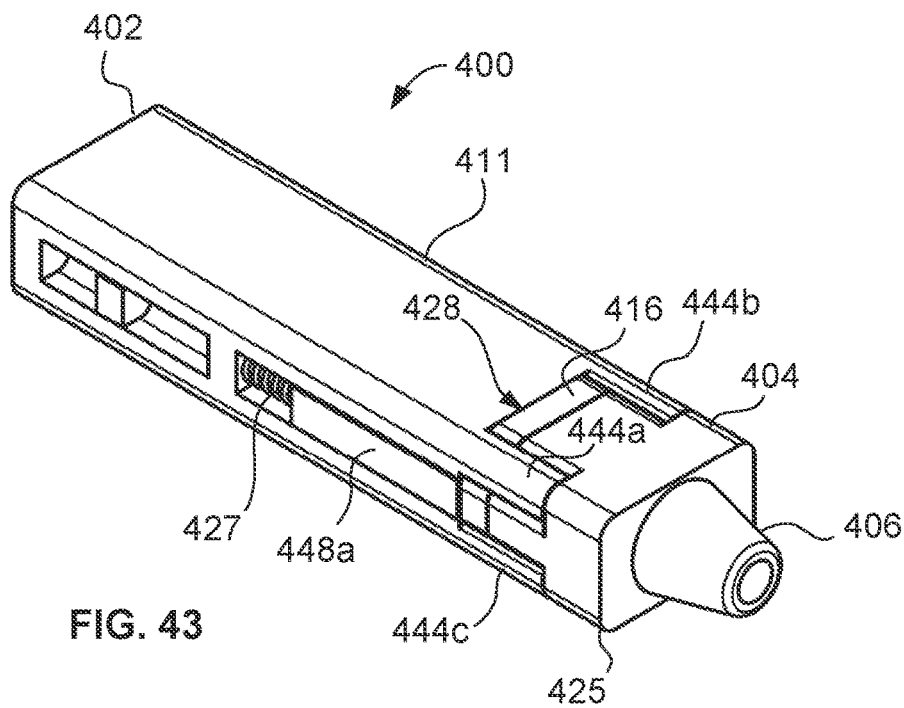
FIGS. 43 to 46 are upper perspective, lower perspective, side and front views, respectively, of an example vaporizer apparatus according to still another embodiment with an outer housing removed and showing a head in an operational position.
Figure 44:
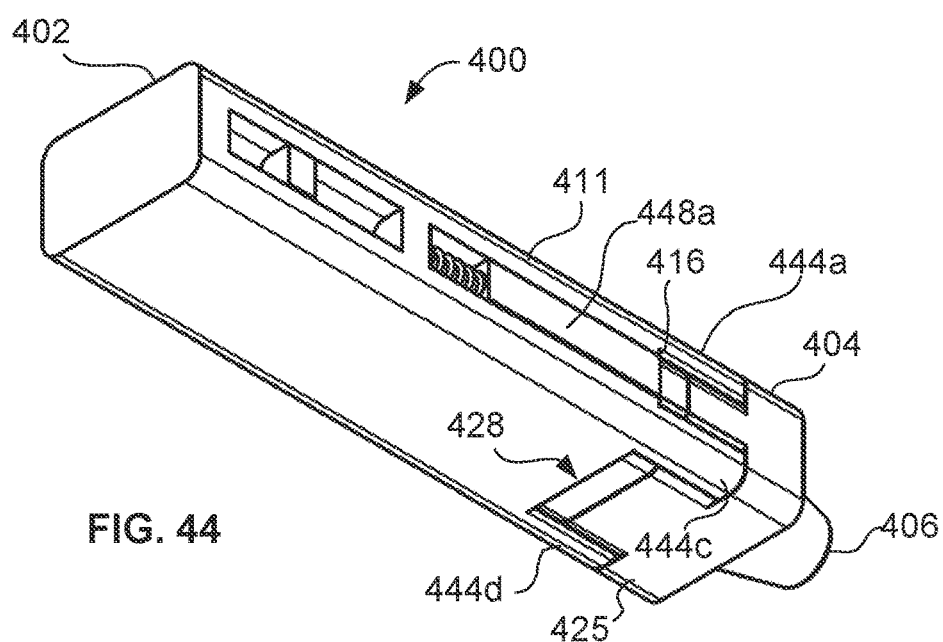
Figures 45, 46:
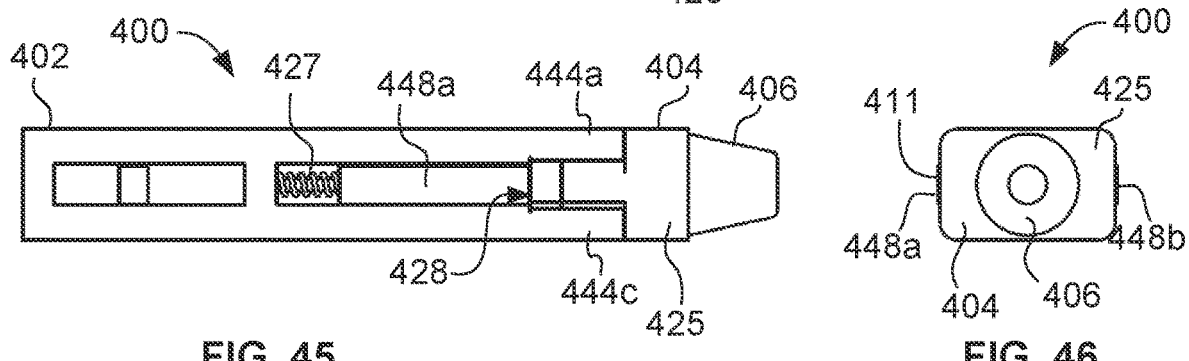
Figure 53:
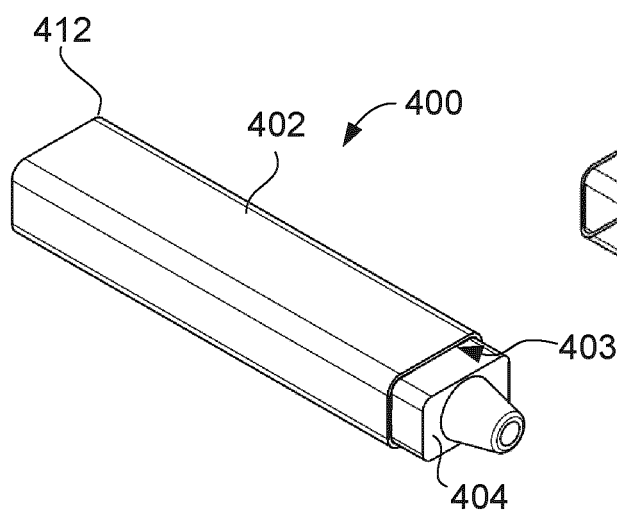
FIGS. 53 and 54 are upper perspective and lower perspective views, respectively, of the vaporizer apparatus of FIGS. 51 and 52 with the head partially ejected from the body.
Figure 54:
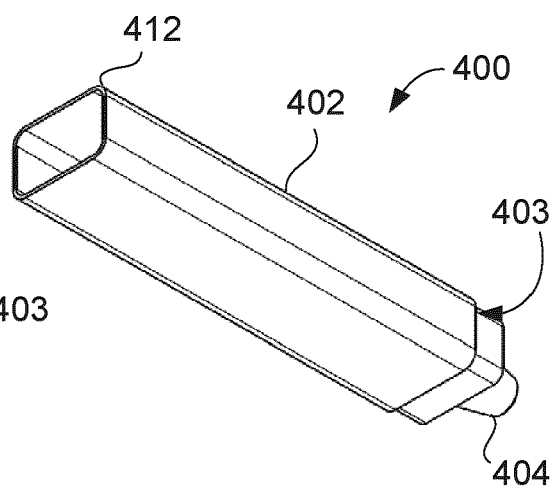

FIGS. 53 and 54 are upper perspective and lower perspective views, respectively, of the vaporizer apparatus 400 with the head still oriented in the same direction as in FIGS. 43 and 46, but with the inner body portion 411 pushed to the forward position so that the head is partially ejected from the body 402 (i.e. extends further from the head than in FIGS. 43 and 46).

Figure 55:
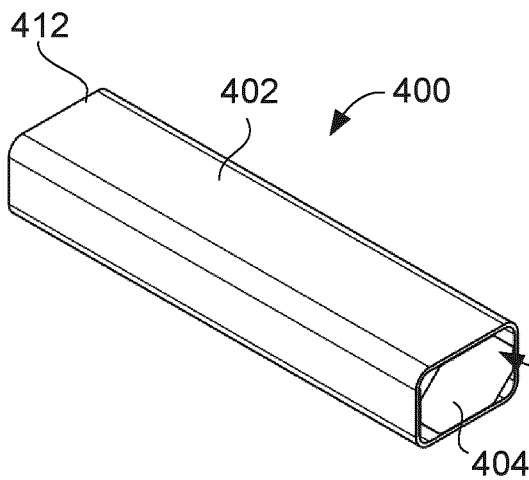
FIGS. 55 and 56 are upper perspective and lower perspective views, respectively, of the vaporizer apparatus of FIGS. 43 to 54 with the head engaged with the body in the non-operational position.
Figure 56:
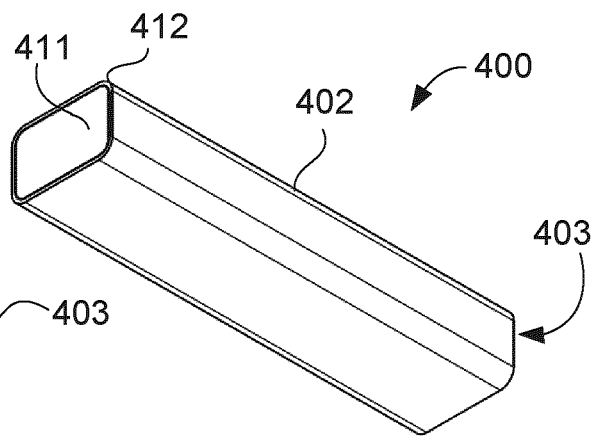

FIGS. 55 and 56 are upper perspective and lower perspective views, respectively, of the vaporizer apparatus 400 with the inner body portion 411 in the rearward (neutral) position relative to the outer housing 412 and the head 404 engaged with the body 402 in the non-operational position.

Figure 57:
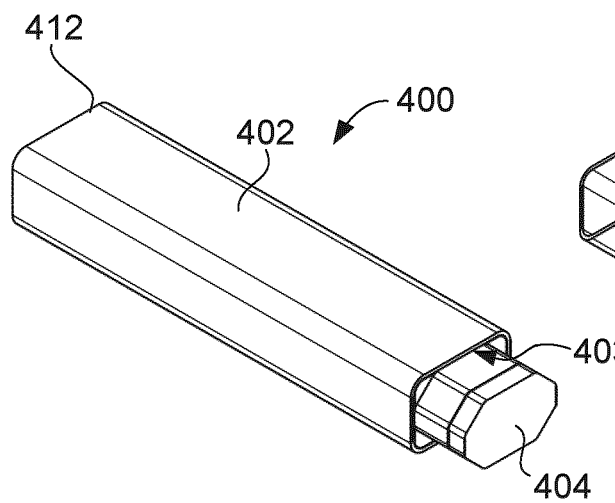
FIGS. 57 and 58 are upper perspective and lower perspective views, respectively, of the vaporizer apparatus of FIGS. 55 and 56 with the head partially ejected from the body.
Figure 58:
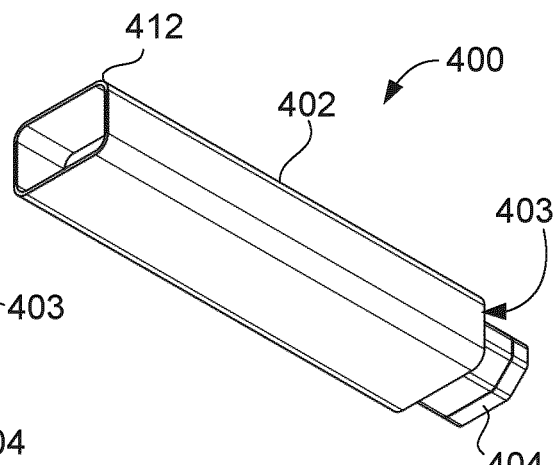

FIGS. 57 and 58 are upper perspective and lower perspective views, respectively, of the vaporizer apparatus 400 with the inner body portion 411 pushed forward relative to the outer housing 412, with the head 404 oriented with the mouthpiece portion 406 (not visible in FIGS. 57 and 58) pointing into the body 402 such that the mouthpiece portion 406 is hidden. As shown, the head 404 extends from the body 402 such that the chamber closure member 416 may be removed in this position without totally removing the head 404.

The vaporizer apparatus 400 may further include one or more air intake openings (not shown) in the head 404 and/or the body 402 that are in fluid communication with the vaporizing chamber and allow air intake into the chamber. The air may then pass from the chamber to the mouthpiece.

According to some embodiments, rather than a completely removable head, the vaporizer apparatus comprises a head that remains connected to the body while being moved between operational and non-operational positions. The head may still releasably engage a docking portion of the body (e.g. an end of the body), but the head may remain connected when disengaged from that docking portion. For example, a hinge connection or other interconnection may remain between the head and the body.

FIGS. 59 to 66 show an example vaporizer apparatus 500 according to still another embodiment. The vaporizer apparatus 500 comprises a body 502 and a head 504 that releasably engages the first end 501 of the body. The head 504 is movable between an operational position and a non-operational position. In this embodiment, the head 504 is collinear with the body 502 and engaged with the first end 501 thereof in the operational position. The head 504 is connected by hinge 510 to the body 502 such that it is pivotable from the operational position to the non-operational position. In the non-operational position, the head 504 is adjacent the body 502 and rotated approximately 180 degrees from the operational position. The body 502 blocks further pivoting of head 504 about hinge 510.

FIGS. 59 to 63 are upper perspective, bottom, side, top and front views, respectively, of the vaporizer apparatus 500 with the head 504 in the operational position. The head comprises a mouthpiece portion 506 that defines suction opening 508 therethrough. During a "vaping" session, a user can position his or her mouth on the mouthpiece portion 506 and inhale, which can cause vapor contained within the head 504 to be drawn through the suction opening 508 and into a user's mouth and lungs for consumption.

The vaporizer apparatus 500 comprises a hinge 510 (shown in FIGS. 60 and 61) that pivotably connects the head 504 to body 502 and allows the head 504 to pivot with respect to the body 502 without completely detaching head 504 from body 502. The hinge 510 in this example is a double hinge, although embodiments are not limited to such hinge connections. Other pivoting connections, such as a virtual hinge mechanism, may also be used.

Optionally, the head 504 may comprise one or more air intake openings to allow air intake in to the interior of head 504 during inhalation by a user on mouthpiece portion 506 and suction opening 508. This example embodiment includes six air intake openings 512. However, the number and form of air intake openings may vary.

The body 502 is elongate and has a first end 501 and opposite second end 503, and the head 504 has a first end 505 and opposite second end 507. The first end 501 forms a docking portion for engaging the head 504, as explained below. During use, the head 504 may be positioned in the operational position. In that position, as shown, the head engages the first end 501 of the body 502 and the mouthpiece portion 506 extends away from body 502. In this embodiment, engaging with the first end 501 comprises docking with the first end 501. In this position, the head 504 and mouthpiece portion 506 are substantially axially aligned and in an end-to-end formation. The mouthpiece portion 506 forms a terminal end of vaporizer apparatus 500. With the head 504 in this "operational position", a user can activate and use the vaporizer apparatus 500.

The vaporizer apparatus 500 in this embodiment includes an optional latch 514 that is usable to releasably secure the head 504 with the first end 501. The latch 514 in this embodiment is mounted to or integrated with the body 502 and engages a catch 515 (shown in FIGS. 64 and 65) in the head 504 to secure head 504 in the "operational position". The latch 514 is releasable to disengage the catch 515 and allow the head 504 to pivot away from the "operational position" about hinge 510, as discussed further below. In other embodiments, the catch may be part of the body 502 and the latch may be integrated with the head 504. Embodiments are not limited to a latch for securing the head in the operational position. For example, snap fitting elements, friction fit or any other suitable securing means may be used rather than the latch 514.

Embodiments are not limited to a pivoting connection (such as a hinge) connecting the head and body of the vaporizer apparatus, and various different mechanical interconnections may be used. For example, and without limitation, the head may be pivotably, slidably, rotatably, and/or extensibly connected to the body. Further, two or more of these types of connections can also be combined together to form the movable connection between the head and the body.

FIGS. 64 to 66 are upper perspective, end, and side views, respectively, of the vaporizer apparatus 500 with the head 504 in the non-operational position. In this embodiment, to move the head 504 to the non-operational position (from the operational position) the head 504 may be disengaged from the first end 501 of the body 502 by releasing latch 514. The head 504 may then be pivoted about the hinge 510 until the head 504 abuts the body 502 (approximately 180 degrees of rotation in this example). The body 502, thus, acts as a stop to block further pivoting of head 504 about hinge 510. In some embodiments, with the head 504 in this non-operational position, the vaporizer apparatus 500 is not useable. The vaporizer apparatus 500 may be disabled anytime that the head 504 is not in the operational position.

The head 504 comprises a vaporizing chamber 516. The chamber 516 in this example has an opening 517 at the first end 505 of the head and is in fluid communication with both the suction opening 508 and the air intake openings 512. When head 504 is in the "operational position", as shown in FIGS. 59 to 63, inhalation on mouthpiece portion 506 by a user draws air into vaporizing chamber 516 through air intake openings 512. The drawn air can mix with vapor formed in vaporizing chamber 516, and air and vapor can exit out of mouthpiece portion 506 through suction opening 508. Vaporizing chamber 516 can be suitably sized and shaped to hold a material to be vaporized. The body 502 comprises a chamber closure member 519 disposed on its first end 501 that covers the opening 517 of the vaporizing chamber 516 when the head 504 engages the first end 501 of the body 502 (i.e. when the first end 505 of the head 504 engages the first end 501 of the body 502).

As shown in FIGS. 64 to 66, moving the head 504 to the non-operational position exposes the vaporizing chamber 516, thereby providing access to the vaporizing chamber 516 in order to position the material to be vaporized (not shown) in vaporizing chamber 516.

As discussed above, the latch 514 may be included to releasably secure the head 504 in the operational position. In some embodiments, the latch 514 may function as a child-lock safety device that prevents unwanted access to vaporizing chamber 516. The latch 514 may be biased to remain in a secured position (held by the catch 515). Thus, accessing the vaporization chamber 516 may require a user to simultaneously release latch 514 (by overcoming the bias) and pivot head 504 away from the operational position. This may comprise two independent actions at the same time, which could be difficult for a child or an unauthorized user to perform. Therefore, the latch 514 of the vaporizer apparatus 500 may decrease the possibility of a child or an unauthorized user using the vaporizer apparatus 500 and/or opening the vaporization chamber 516 and accessing the vaporization materials contained within the vaporization chamber 516.

In some embodiments, vaporizing chamber 516 is further operatively connected to a heating element (not shown) that is configured to, upon being activated, heat the vaporizing chamber to vaporize the material held therein. In some embodiments, the heating element comprises a heating coil (not shown) that can heat vaporizing chamber 516. The heating element may, for example, comprise one or more metal, ceramic or glass heating coils. The vaporizer apparatus 500 may further comprise a power source, such as a battery (not shown) electrically connected to the heating element. In some embodiments, the heating element, when provided with electrical power from the power source, provides heat to the vaporizing materials contained within vaporizing chamber 516 to emit a vapor. The vaporizer apparatus may further comprise a processor coupled to the heating element and power source to control the activation of the heating element.

In some embodiments, the heating element can be activated by a user by means of a user interface element (e.g. a button) that is operatively connected to heating element and/or the processor. The user interface may be manipulated by a user to activate the heating element. In the example embodiment of FIGS. 59 to 66, the activation mechanism comprises a button 520 mounted to the vaporizer apparatus 500 that is pressable by a user to activate the heating element. In some embodiments, pressing button 520 may also control temperature settings of heating element. In some embodiments, pressing button 520 can cause electrical power to flow from the power source to the heating element to create heat in vaporizing chamber 516. However, different activation mechanism could be employed to activate the heating element and embodiments are not limited to a button. For example, in other embodiments, the vaporizer apparatus may include a sensor that detects air being drawn through the mouthpiece portion and activates the heating element responsive to the detection. Thus, a user may activate the vaporizer apparatus by inhaling from the mouthpiece portion.

In some embodiments, the activation mechanism may comprise a user interface that is displayed on a user operated computer device, such as a general purpose computer, a laptop computer, a tablet computer, or a smartphone. In some embodiments, the user interface can be manipulated by a user to activate the heating element wherein the user operated computer device is in communication to the vaporizer through a communication network. In some embodiments, the user interface can be displayed on the user operated computer device upon the user entering a password to the user operated computer or other authentication procedure that is entered on the computer device. Such a process can decrease the possibility that vaporizer apparatus 500 will be either inadvertently activated, or activated by a child (e.g. a child-lock safety device). In some embodiments, the communication network can be a wireless communication network. In some embodiments, the wireless communication network can comprise one of: a Bluetooth network, a Wi-Fi network, a near field communication network, or another type of wireless communication network.

In some embodiments, the vaporizer apparatus 500 further comprises one or more biasing elements that biases the head 504 toward the operational position. In some embodiments, the biasing element comprises at least one magnet positioned to hold the head 504 in the operational position. For example, the first at least one magnet may comprise a first magnet 522 (shown in FIG. 64) embedded in the first end 501 of the body 502. A ferrous metal piece 524 (shown in FIG. 64) is disposed in the first end 505 of the head 504 and positioned to engage the magnet 522. An attractive magnetic force between the magnet 522 and metal piece 524 may bias the head 504 to move toward and remain engaged with the first end 501 of the body 502 (i.e. in the operational position). In other embodiments, a second magnet may be used in place of the metal piece 524.

Figure 60:
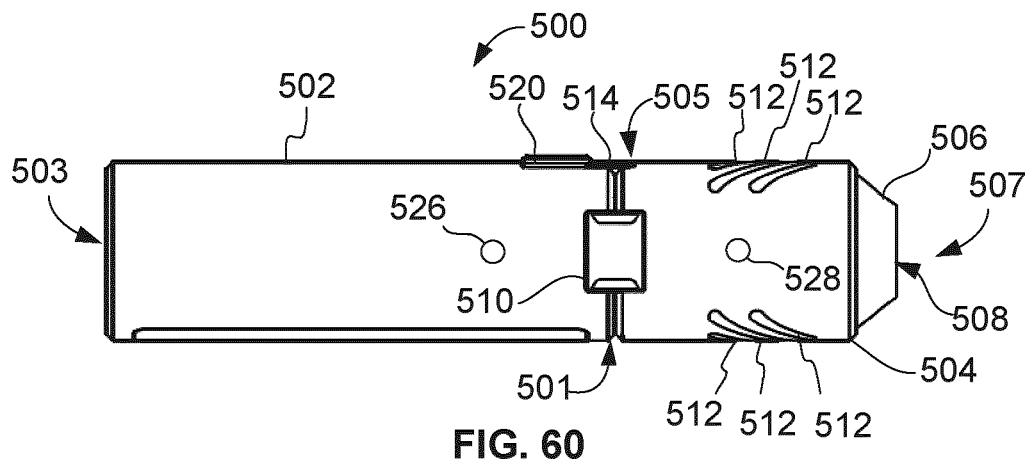
Figure 61:
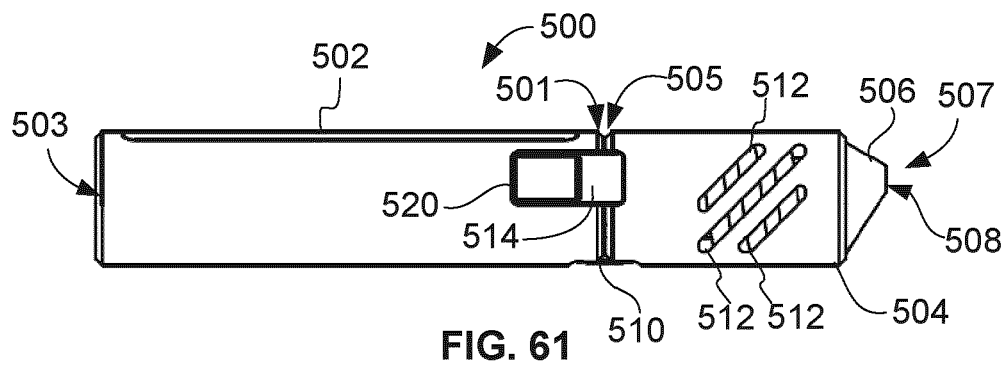
Figure 62:
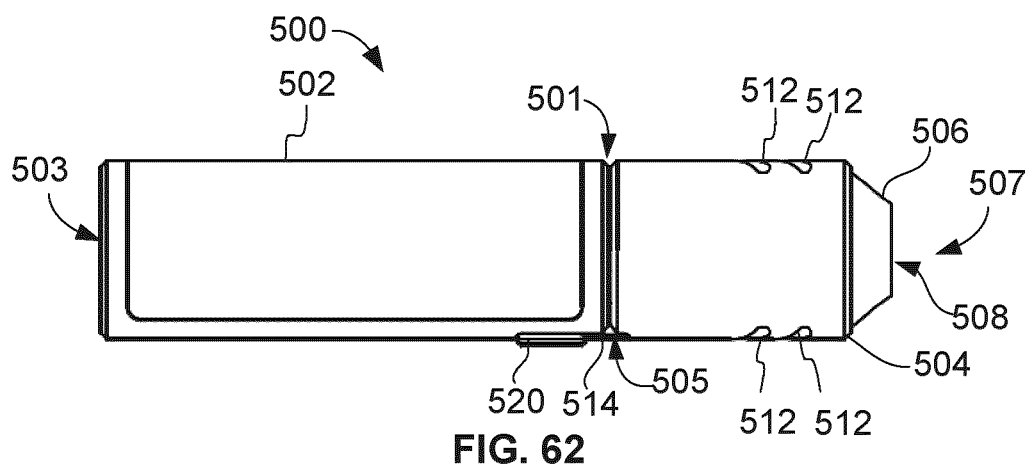
Figure 63:
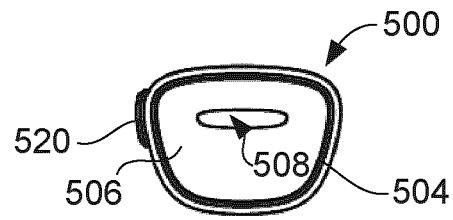
Figure 67:
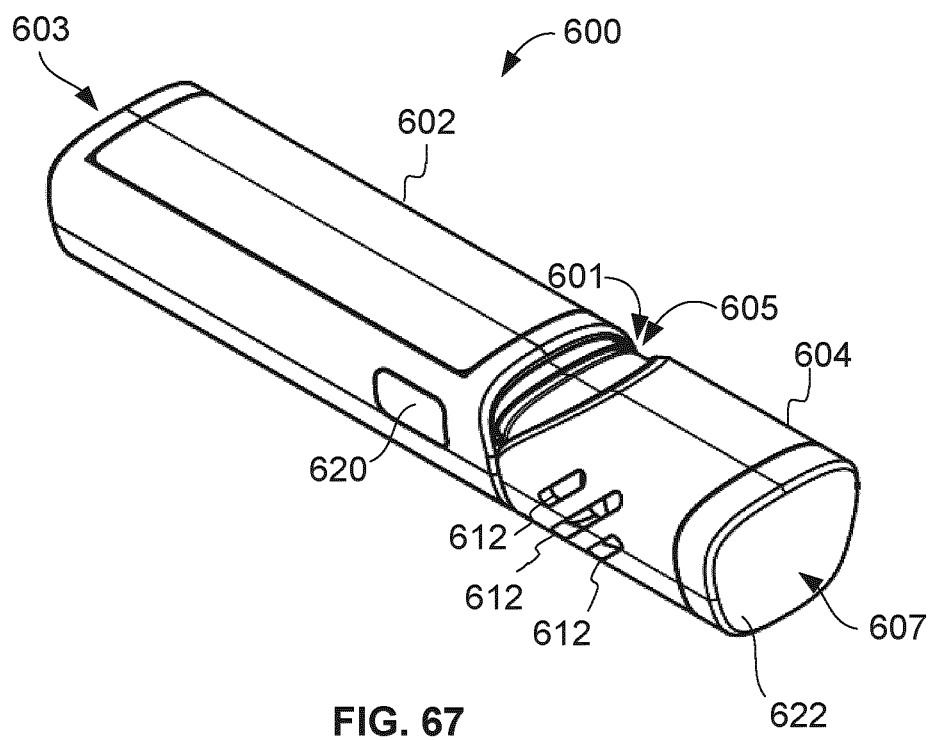
FIGS. 67 to 71 are upper perspective, bottom, side, top and front views, respectively, of an example vaporizer apparatus according to still another embodiment with a pivoting head shown in a non-operational position.
Figure 68:
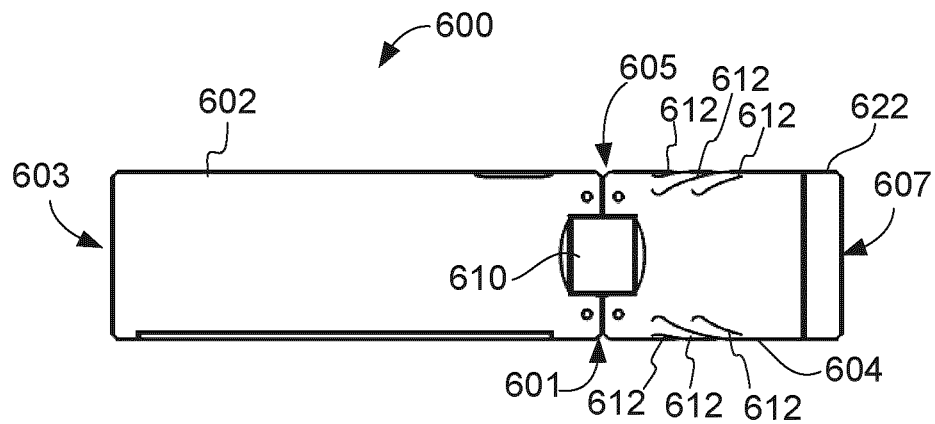
Figure 69:
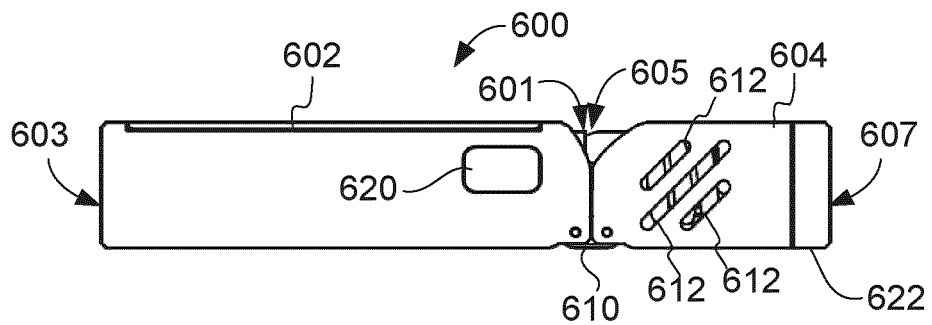
Figure 70:
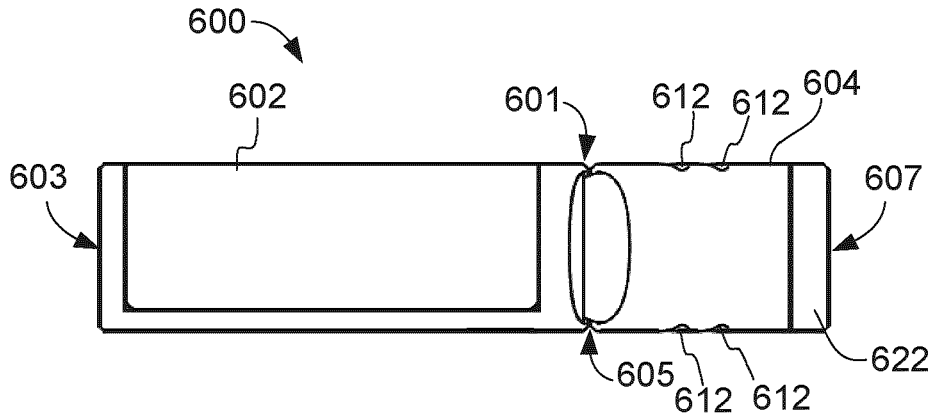
Figure 71:
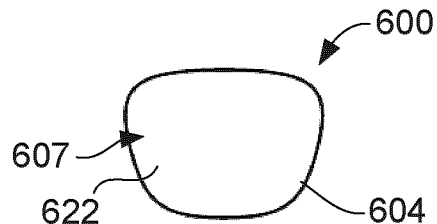

In some embodiments, the vaporizer apparatus 500 further comprises a second biasing element that biases the head 504 toward the non-operational position. The second biasing element may include a second at least one magnet. For example, as shown in FIG. 60, the second at least one magnet may comprise a second magnet 526 embedded on a face of the body 502. A second metal piece 528 is disposed in a corresponding face of the head 504 and positioned to engage the second magnet 526 when the faces of the head 504 and body 502 are adjacent in the non-operational position. An attractive magnetic force between the second magnet 526 and the second metal piece 528 may bias the head 504 to move toward and/or remain engaged with the bottom face of the body 502 (i.e. in the non-operational position). In other embodiments, still another magnet may be used in place of the second metal piece 528.

Embodiments are not limited to magnets as biasing elements, and other biasing elements such as springs may be used. For example, the vaporizer apparatus 500 may include one or more springs to bias the head to the operational position, the non-operational position, or both. For example, a first at least one spring may be positioned to urge the head to the operational position, and/or a second at least one spring may be positioned to urge the head to the non-operational position. The one or more springs may be positioned near the hinge 510. As another example, the hinge 510 may comprise an assembly that includes the one or more springs (or other biasing elements). The biasing elements may be omitted in other embodiments. A mix of different types of biasing elements may also be used in still further embodiments.

With reference to FIG. 66, hinge 510 is arranged on a bottom face 525 of the body 502 such that the head 504 initially pivots downward from the operational position and then abuts the bottom face 525 in the non-operational position. However, in other embodiments, the hinge may be arranged to pivot the head in other directions (e.g. upward, to the side, etc.).

FIGS. 67 to 74 show an example vaporizer apparatus 600 according to yet another embodiment. The vaporizer apparatus 600 comprises a body 602 and a head 604. The body 602 has a first end 601 and a second end 603, and the head 604 has a first end 605 and a second end 607. As in the previous embodiment, the vaporizer apparatus comprises a hinge 610, and the head 604 is pivotable between operational and non-operational positions. The vaporizer apparatus 600 may also include a latch to hold the head in the non-operational or operational position.

The head 604 and is movable between the operational position and a non-operational position. In this embodiment, the head 604 is collinear with the body 602 and engaged with the end 601 thereof in the non-operational position. The head is pivotable from the non-operational position to the operational position (and vice versa). In the operational position, the head 604 is adjacent the body 602 and rotated approximately 180 degrees from the non-operational position. The body 602 blocks further pivoting of head 604 about hinge 610.

FIGS. 67 to 71 show the head 604 in the non-operational position for this embodiment. In the non-operational position, the head 604 is collinear with and extends away from the body 602, and the first end 605 of the head 604 releasably engages the first end 601 of the body 602. The head 604 comprises a mouthpiece portion 606 (shown in FIGS. 72 to 74) at its first end 605. The mouthpiece portion 606 is at least partially received in the first end of the body 601 and at least partially covered by the first end 601 of the body in the non-operational position. This configuration is in contrast to the embodiment of FIGS. 59 to 66 where the operational position has the head 504 and body 502 collinear and abutting. Thus, embodiments are not limited to embodiments where the head is collinear with the body for the operational position.

Figure 72:
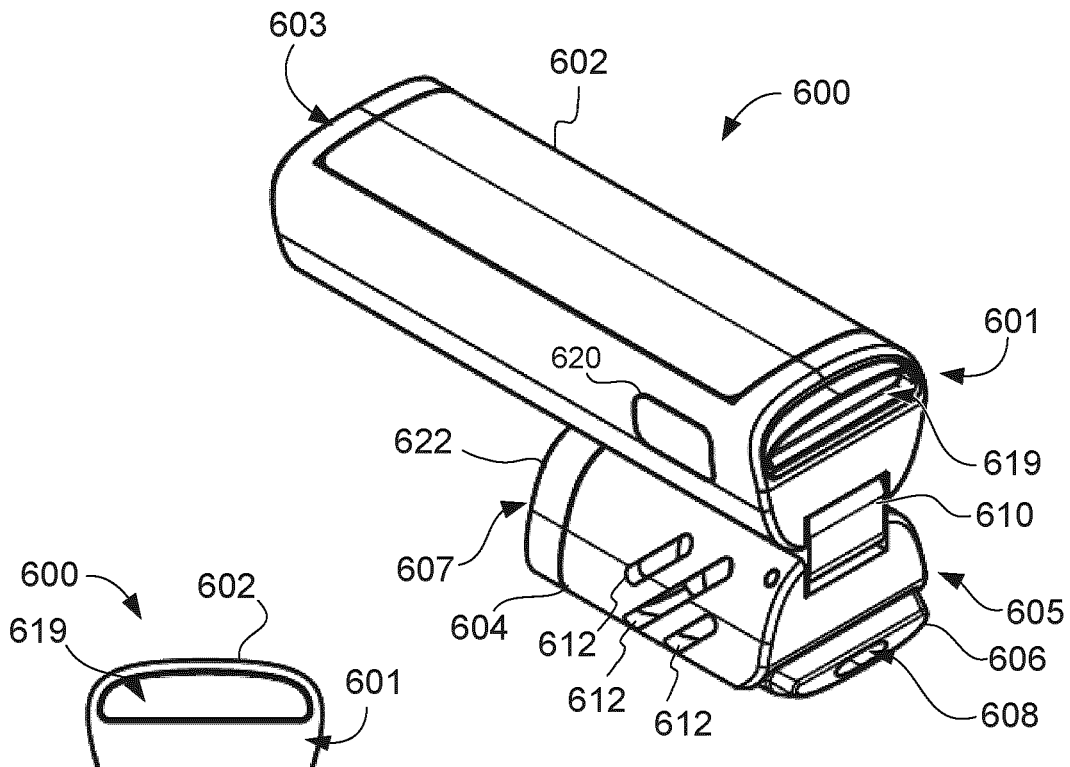
FIGS. 72 to 74 are upper perspective, end, and side views, respectively, of the vaporizer apparatus of FIGS. 67 to 71 with the head pivoted to an operational position.
Figure 73:
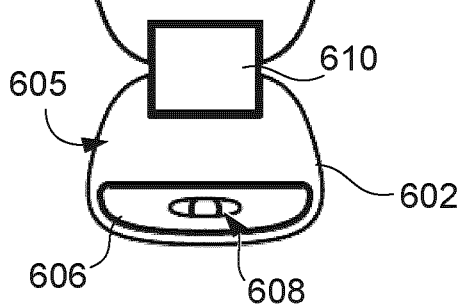
Figure 74:
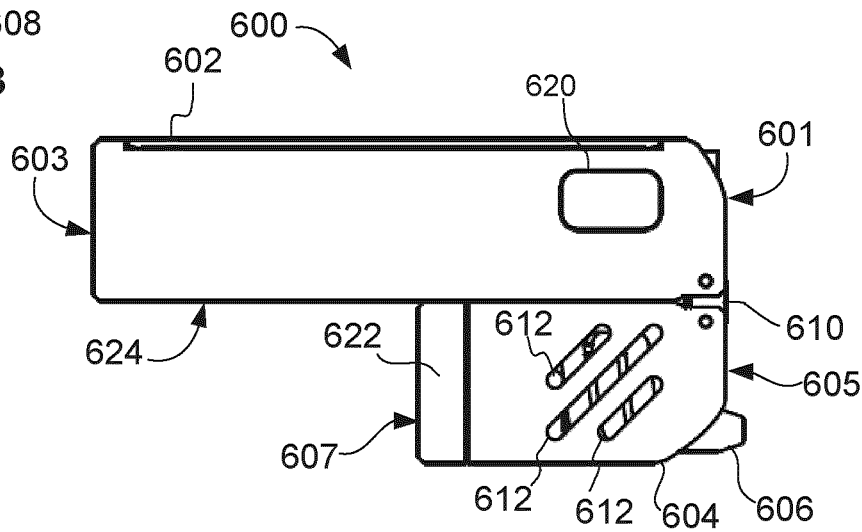

FIGS. 72 to 74 show the vaporizer 600 with head 604 in the "operational position". To move the head 604 from the non-operational position to the operational position, the head 604 is rotated approximately 180 degrees about the hinge 610 until it is substantially parallel to and adjacent the body 602. This rotation disengages the head 604 from the first end 601 of the body 602. The body 602 may act as a stop preventing further pivoting of the head 604. Moving the head 604 into this position exposes the mouthpiece portion 606 of the head 604 such that the vaporizer apparatus 600 is useable. That is, when the mouthpiece portion 606 and a suction opening 608 therein are exposed a user may position his or her mouth on the mouthpiece portion 606 to use the vaporizer apparatus 600.

In some embodiments, the body 602 defines a mouthpiece docking recess 619 at or near the first end 601 that at least partially receives the mouthpiece portion 606 of the head 604 in the non-operational position. The mouthpiece docking recess 619 may be suitably sized and positioned on body 602 so as to receive at least a portion mouthpiece portion 606. Partial or complete coverage of mouthpiece portion 606 may provide some protection to the mouthpiece portion 606 when vaporizer apparatus 600 is in the non-operational position, potentially making vaporizer 600 more hygienic to use and block unwanted material from entering mouthpiece portion 606.

In this embodiment, the head 604 comprises a vaporizing chamber (not shown) therein that is covered by vaporizing chamber closure member 622 at the second end 607 of the head 604. Access to vaporizing chamber can be achieved by moving or removing the vaporizing chamber closure member 622 from the head 604 so that materials for vaporizing can be positioned in vaporizing chamber. In some embodiments, the vaporizing chamber closure member 622 can be removed when the head 604 is in the "non-operational position" allowing access to vaporizing chamber only when the vaporizer apparatus 600 is not useable.

Similar to other embodiments described herein, when the head 604 is in the "operational position", inhalation on mouthpiece portion 606 can draw air into vaporizing chamber (through air intake openings 612 in this embodiment). The drawn air can mix with vapor formed in vaporizing chamber, and air and vapor exit out of the mouthpiece portion 606 through the suction opening 608.

In some embodiments, button 620 can be mounted on vaporizer 600 that is operatively connected to a heating element. Button 620 can be pressed to activate the heating element in order to emit a vapor from the vaporization materials. However, any activation means could be employed to activate the heating element and pressing a button to activate the heating element is not a limitation to the disclosure.

Additionally, in some embodiments, heating element may only be activated when the head 604 is in the operational position shown in FIGS. 72 to 74. In other words, vaporizer 600, in some embodiments, may not be turned on when head 604 is in the non-operational position, thereby decreasing the possibility of inadvertent inactivation. In some embodiments, an operative connection between button 620 and heating element is complete only when head 604 is in the operational position. In some embodiments, vaporizer 600 includes a position sensor (not shown) mounted on head 604 that senses the position of head 604 with respect to body 602. A position sensor may provide output that enables the heating element to be activated when the head 604 is in the operational position and/or disables the heating element when the head 604 is not in the operational position.

In some embodiments, the vaporizer apparatus 600 may only be activated by both moving the head 604 into the operational position and pressing the button 620. This may decrease the possibility that vaporizer 600 will be either inadvertently activated, or activated by a child. Therefore, a user may be relatively confident that vaporizer apparatus 600 is not going to be activated when the head 604 is in the non-operational position in some embodiments. Optionally, activation of vaporizer 600 can be achieved by simultaneously pressing button 620 and pivoting head 604 to the operational position.

With reference to FIG. 74, hinge 610 is arranged on a bottom face 624 of the body 602 such that the head 604 initially pivots downward from the non-operational position and then abuts the bottom face 624 in the non-operational position. However, in other embodiments, the hinge may be arranged to pivot the head in other directions (e.g. upward, to the side, etc.).

FIGS. 75 to 81 show another example vaporizer apparatus 700 according to some embodiments. The vaporizer apparatus 700 comprises a body 702 and a head 704 that releasably engages and end 701 of the body. The head 704 and is movable between an operational position and a non-operational position. In this embodiment, the head 704 is collinear with the body 702 and engaged with the end 701 thereof in the operational position. The head 704 is connected by hinge 710 to the body 702 such that it is pivotable from the operational position to the non-operational position.

Figure 75:
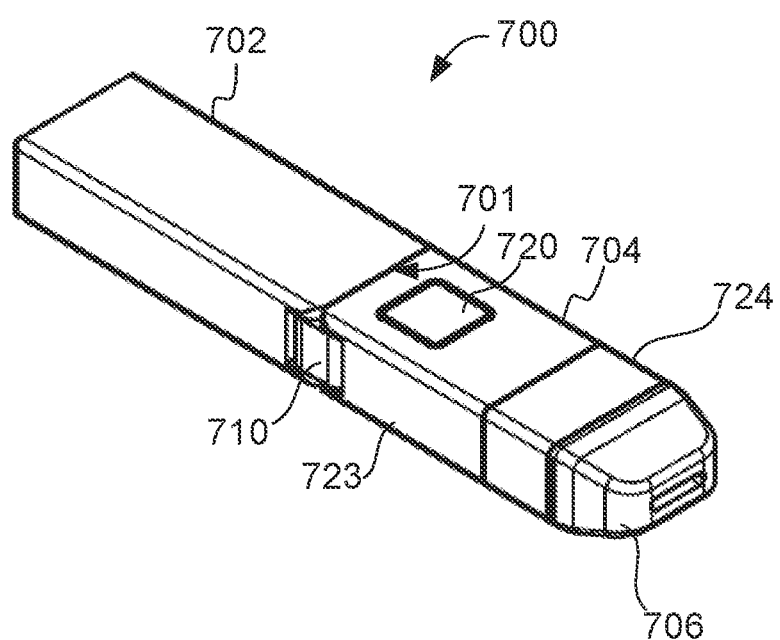
FIGS. 75 to 77 are upper perspective, top and side views, respectively, of an example vaporizer apparatus according to yet another embodiment having a removable cartridge and a pivoting head shown in an operational position.
Figure 76:
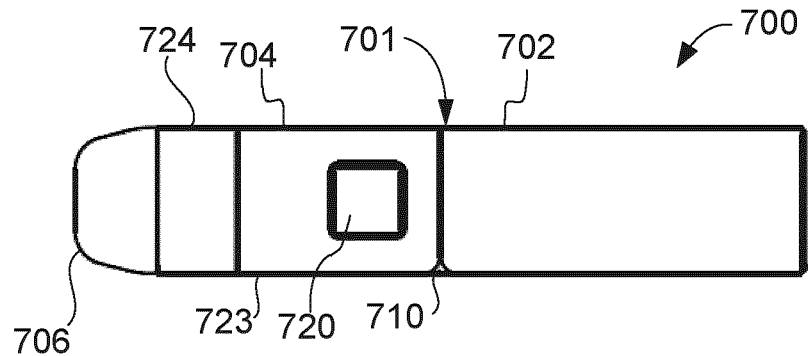
Figure 77:
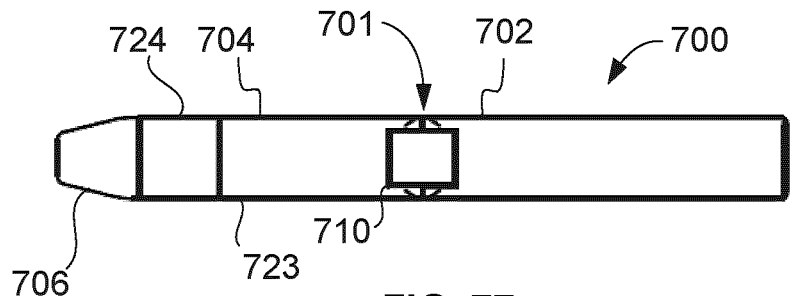

FIGS. 75 to 77 are upper perspective, top and side views, respectively, of the vaporizer apparatus 700 with head 704 in the operational position. In that position, the vaporizer apparatus 700 is usable for vaping, similar to other embodiments described herein (i.e. a heating element is activatable, and vapor may be drawn through the mouthpiece portion 706. When the head 704 is not in the operational position, the vaporizer is not useable and may be relatively convenient to store or transport between "vaping" sessions.

In this embodiment, the vaporizer apparatus 700 is modular in that it includes a removable and replaceable cartridge 724. In this embodiment, the head 704 comprises a first portion 723 that is hingedly attached to the body 702. The head 704 further comprises the cartridge 724. The mouthpiece portion 706 is integrated with the removable cartridge 724 in this embodiment, but the mouthpiece may be separate and removable from the cartridge 724 in other embodiments. Though not specifically shown, the removable cartridge 724 may include a reservoir to hold a fluid (e.g. oil) to be vaporized, a vaporizing chamber that receives the fluid from the reservoir (e.g. via a wick), and the mouthpiece portion 706. The removable cartridge 724 may be conveniently swapped with other cartridges. Each cartridge may include a respective reservoir (e.g. for oil), vaporizing chamber, vaporization material, and mouthpiece portion. Thus, each cartridge, when selected by a user, may be attached to the first portion 723 of the head 704 and be ready to use for a vaping session. The user may, therefore, conveniently customize the vaporizer apparatus 700, including changing the material to be vaped for different sessions.

Similar to above, the heating element can be activated by pressing button 720 mounted to vaporizer 700.

Figure 78:
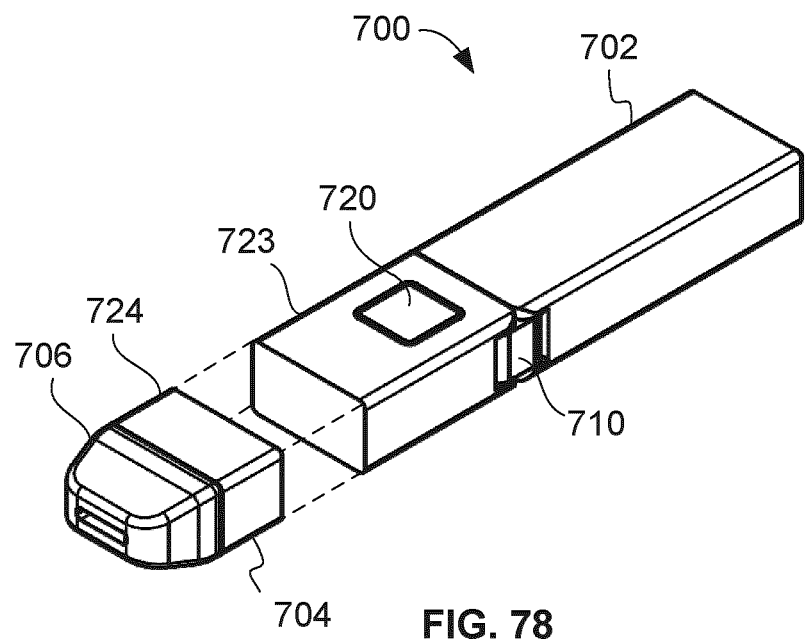
FIG. 78 is an exploded upper perspective view of the vaporizer apparatus of FIGS. 75 to 77.

FIG. 78 is an exploded perspective view of the vaporizer apparatus 700 showing the cartridge 724 removed from the first portion 723 of the head 704. Though not shown, the cartridge 724 and/or first portion 723 may include attachment means to releasably attach the cartridge 724 to the first portion. Any suitable means may be used to secure the cartridge 724 to the first portion 723. Though not shown, the cartridge 724 and the first portion 723 may further include one or more operable connections when engaged (such as electrical power or signal connections, air flow connections, etc.).

In some embodiments, removable cartridge 724 can be attached to head 704 by inserting at least a portion of removable cartridge 724 into vaporizing chamber (not shown). In some embodiments, the at least a portion of removable cartridge 724 can comprise the vaporizing material such that the vaporizing material can be heated within vaporizing chamber when at least a portion of the removable cartridge 724 is positioned in vaporizing chamber. In some embodiments, cartridge 724 can have a material to be vaporized prepackaged into cartridge 724 so that a user does need to handle any loose material to use vaporizer 700. In some embodiments, removable cartridge 724 can be disposable after a portion of the material has been vaporized. In some embodiments, removable cartridge 724 can be re-useable after a portion of the material has been vaporized.

In some embodiments, removable cartridge 724 can comprise a vaporizing chamber (not shown), mouthpiece portion 706, and a vaporizing material (not shown) positioned within the vaporizing chamber. In some embodiments, replacing removable cartridge 724 can also result in a replacement to vaporizing chamber. In some embodiments, replacing cartridge 724 can result in a change in the type of vaporizing chamber used by vaporizer 700. For example, in some embodiments, one cartridge 724 having a dry herb oven as a vaporizing chamber can be replaced with the cartridge 724 having a liquid vaporizer as a vaporizing chamber. In some embodiments, replacing vaporizing chamber can result in a change in the type of vaporizing material used by vaporizer 700.

Figure 79:
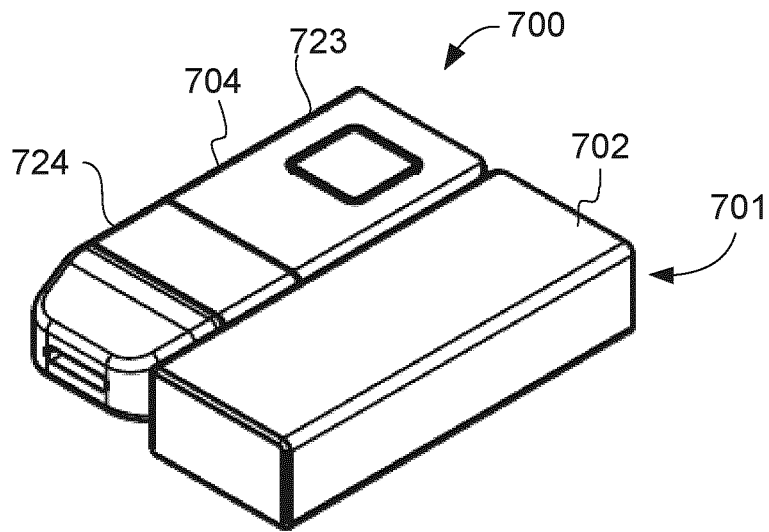
FIGS. 79 to 81 are upper perspective, top, and end views, respectively, of the vaporizer apparatus of FIGS. 75 to 81 with the head pivoted to the non-operational position.
Figure 80:
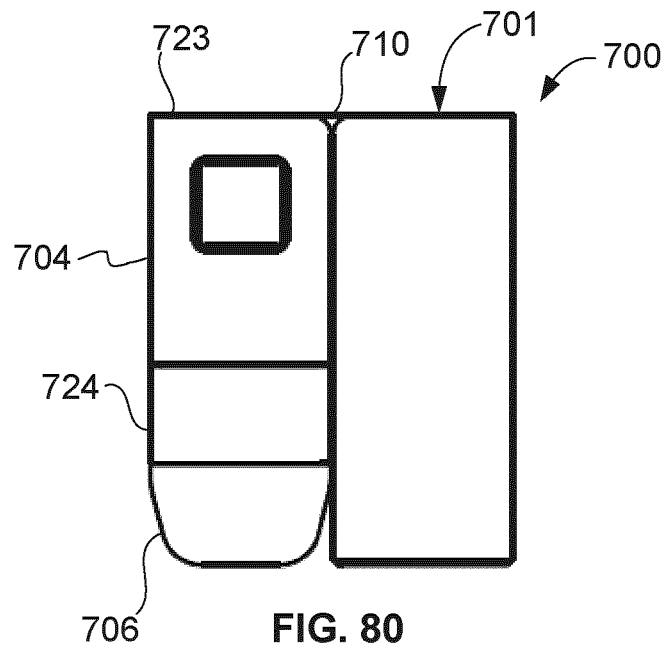
Figure 81:
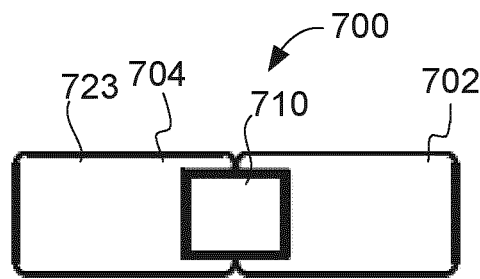

FIGS. 79 to 81 are upper perspective, top and end views, respectively, of the vaporizer apparatus 700 with the head 704 rotated to the non-operational position. In this embodiment, the hinge 710 is positioned on a side of the apparatus 700 so that the head 704 pivots in a horizontal direction rather than upwards/downwards. In the non-operational position, the head 704 is adjacent the body 702 and rotated approximately 180 degrees from the operational position. The body 702 blocks further pivoting of head 704 about hinge 710.

FIGS. 82 to 89 show another example vaporizer apparatus 800 according to some embodiments. The vaporizer apparatus 800 comprises a body 802 and a head 804 (shown in FIGS. 85 to 87) integrated with the body 802. The vaporizer apparatus 800 comprises a removable cap 826 that releasably engages the vaporizer apparatus 800 in a "non-operational position" and an "operational position". The body 802 comprises a first end 801 (referred to as "mouthpiece end 801" herein) and a second end 803 opposite to the mouthpiece end 801.

Figure 82:
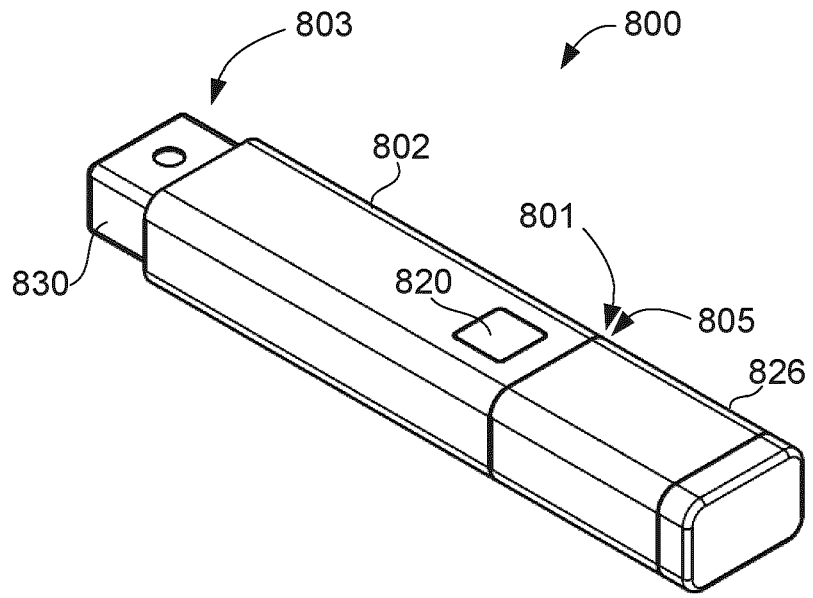
FIGS. 82 to 84 are upper perspective, top and side views, respectively, of an example vaporizer apparatus according to another embodiment with a cap positioned on a body in a non-operational position.
Figure 83:
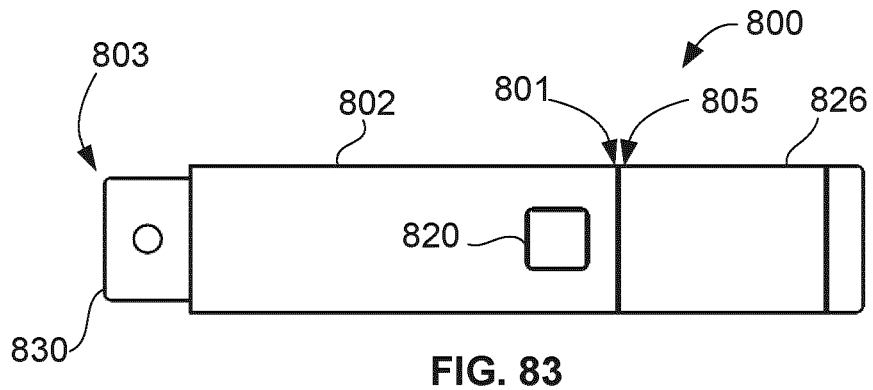
Figure 84:
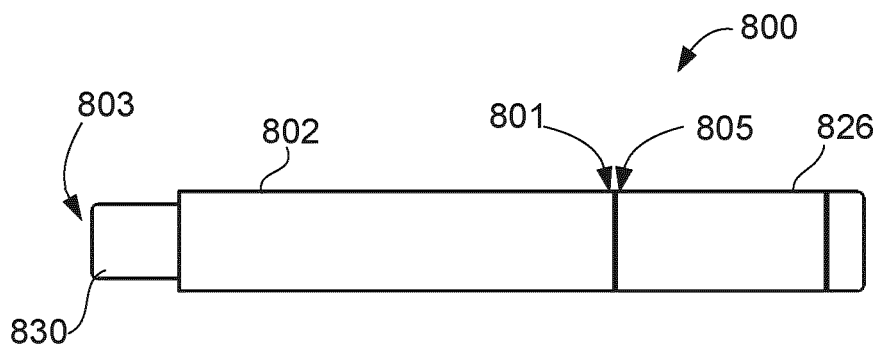

FIGS. 82 to 84 are upper perspective, top and side views, respectively, of the vaporizer apparatus 800 with the cap 826 positioned on body 802 at the mouthpiece end 801 and a second end 803 opposite to the mouthpiece end 801, which is the non-operational position. In the non-operational position, the mouthpiece 806 at the mouthpiece end 801 is covered by the cap 826.

Figure 85:
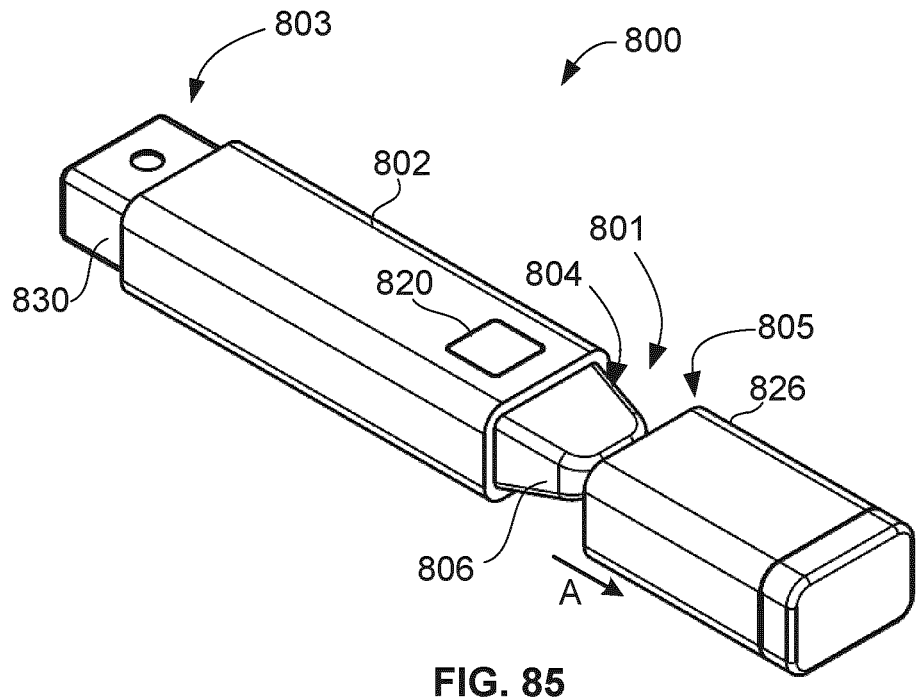
FIGS. 85 to 87 are perspective exploded, top exploded and side exploded views, respectively of the vaporizer apparatus of FIGS. 82 to 84 showing the cap removed from the "non-operational position"
Figure 86:
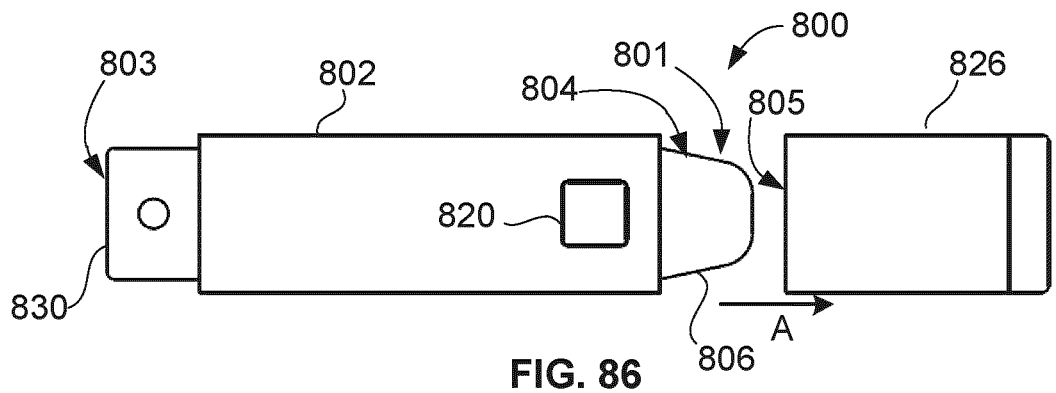
Figure 87:
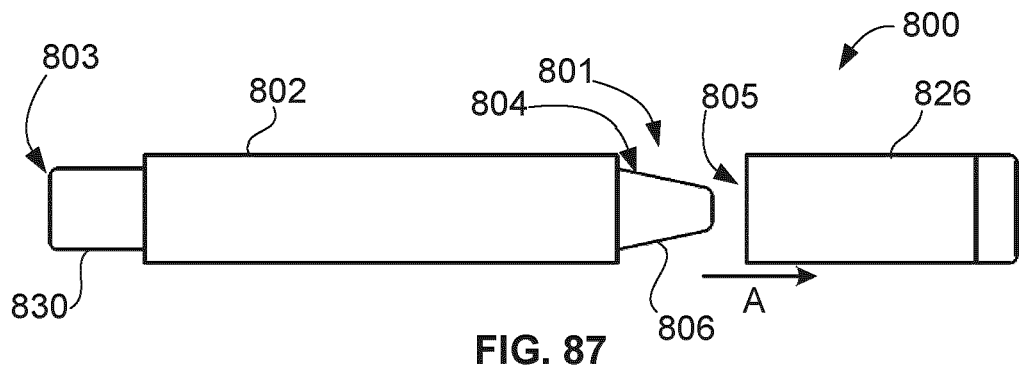

FIGS. 85 to 87 are perspective exploded, top exploded and side exploded views, respectively show cap 826 removed from the "non-operational position" on body 802. The cap 826 is removed by pulling cap 826 in direction "A" (indicated by an arrow) from body 802, thereby revealing mouthpiece portion 806 formed on body 802. In some embodiments, mouthpiece portion 806 can be at least partially covered by cap 826 when cap 826 is in the "non-operational position". In some embodiments, mouthpiece portion 806 can be received in a docking portion 828 formed in the cap 826 when cap 826 is in the "non-operational position". The docking portion 828 is formed by the open end 805 of the cap 826 and is suitably sized and positioned to receive at least a portion of the mouthpiece portion 806 when cap 826 is in the "non-operational position". Partial or complete coverage of mouthpiece portion 806 may provide some protection to the mouthpiece portion 806 when vaporizer apparatus 800 is not being used, potentially making vaporizer apparatus 800 more hygienic to use and block unwanted material from entering mouthpiece portion 806.

As shown, the second end 803 of the body 802 comprises an extension 830 that acts as a second docking portion for the cap 826. That is, the extension 830 is shaped complementary to the docking portion 828 of the open end 805 of the cap 826 so that the cap snuggly fits over the extension 830. The cap 826 may, thus, placed over the extension 830 to thereby engage the second end 803 of the body and hold the cap 826 in the operational position (shown in FIG. 89).

Figure 88:
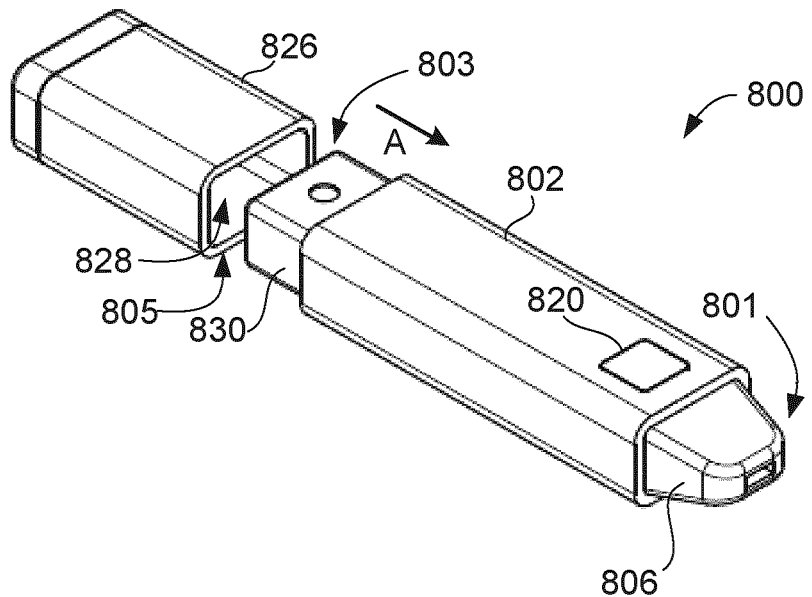
FIG. 88 is an upper perspective view of the vaporizer apparatus of FIGS. 82 to 87 showing the cap removed from the body and positioned to be placed on a second end of the body in an operational position.
Figure 89:
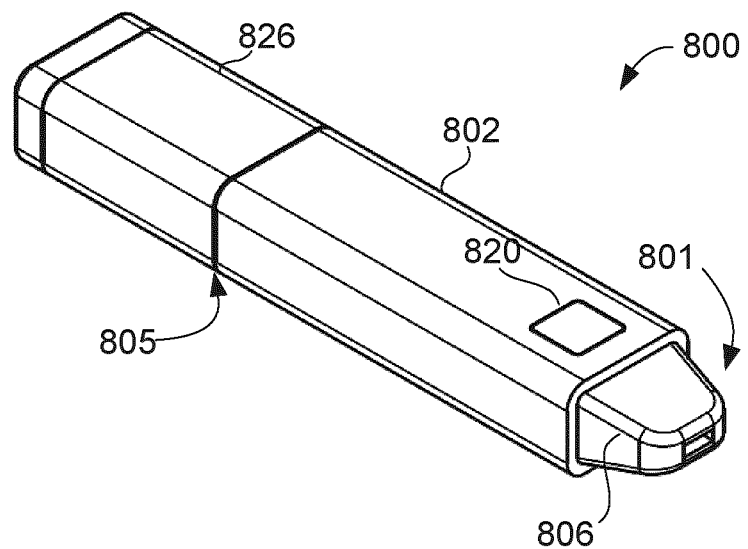
FIG. 89 is an upper perspective view of the vaporizer apparatus of FIGS. 82 to 88 with the cap in the operational position.

FIGS. 88 and 89 show cap 826 being positioned on body 802 in the operational position by pushing cap 826 in direction "A" over body extension 830. Docking portion 828 formed on cap 826 is suitably sized and positioned so as to receive at least a portion of body extension 830 when cap 826 is in the operational position shown in FIG. 89. Similar to before, when cap 826 is in the operational position, inhalation on mouthpiece portion 806 by a user can occur to draw a vapor from vaporizer apparatus 800 out of suction opening 808.

Similar to before, heating element, in some embodiments, can be activated by pressing button 820 mounted to vaporizer apparatus 800. Additionally, in some embodiments, heating element may only be activated when the cap 826 is in the operational position, as shown in FIG. 89. In other words, vaporizer apparatus 800, in some embodiments, may not be turned on when cap 826 is in the "non-operational position", thereby decreasing the possibility of inadvertent inactivation. In some embodiments, cap 826 can comprise vaporizing chamber. In some embodiments, cap 826 can comprise a dry herb oven for vaporizing a plant material (not shown).

In some embodiments, vaporizer can be activated only by both moving the cap 826 from the "non-operational position" to the "operational position" and pressing button 820.

Figure 90:
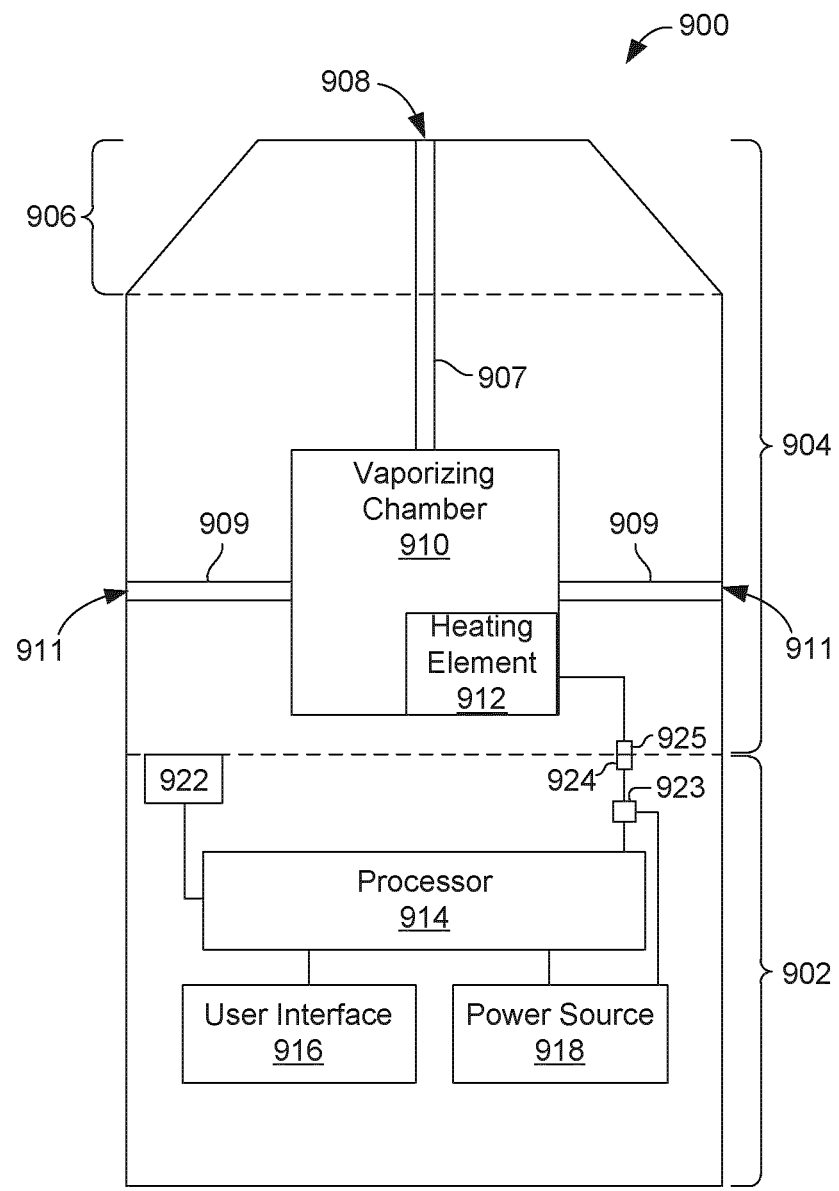
FIG. 90 is a functional block diagram of another example vaporizer apparatus according to some embodiments.

FIG. 90 is a functional block diagram of a vaporizer apparatus 900 according to some embodiments. The vaporizer apparatus 900 comprises body 902 and head 904. The head 904 may releasably engages the body 902 and may be movable between operational and non-operational positions. The head 904 and body 902 may have one or more features of the example heads and bodies of vaporizer apparatuses described above with reference to FIGS. 1 to 89, or combinations thereof. Likewise, the embodiments described above with reference to FIGS. 1 to 89 may implement one or more features discussed below with reference to FIG. 90.

The head 904 includes a vaporizing chamber 910 and a heating element 912 coupled to the chamber to vaporize material therein. The heating element 912 may be positioned at least partially within the chamber 910. The heating element 912 may be a coiled filament or any other suitable element for generating heat to vaporize the material in the chamber 910.

The body 902 includes a power source 918, such as a battery, and optionally includes one or more user interface elements 916. The one or more user interface elements 916 may comprise a control such as a button. In this example, the power source 918 and user interface elements 916 are operatively connected to a processor 914. The processor 914 may process input from the user interface elements 916 and activate the heating element 912 by providing power from the power source to the heating element 912 accordingly. For example, the body 902 may comprise a switch 923 that is activated by the processor to provide power to the heating element 912.

The body 902 may comprise a first operative connection element 924 (such as an electrical connector). The head 904 may comprise a second operative connection element 925 (such as an electrical connector). The first and second operative connection elements may engage each other as shown in FIG. 90 when the head 904 is in the operational position. The first and second operative connection elements 924 and 925 may provide an electrical connection between the head 904 and the body to allow power to be transferred to the heating element 912 from the power source 918. Removing the head 904 from the operational position may disengage the operative connection elements 924 and 925 such that the heating element 912 is disabled.

The body 902 or head 904 may optionally further comprise a sensor 922 arranged to sense when the head 904 is in the operational position and generate an output to enable the heating element 912 accordingly. As another option, the sensor 922 may generate output to disable the heating element 912 when the head is not in the operational position. While the sensor 922 is shown in the body 902 and coupled to the processor 914 in FIG. 90, the sensor 922 may be in the head 904 in other embodiments. More than one sensor may be used in the head 904 and/or body 902 in other embodiments.

The head 904 may include one or more air intake openings 911 that are in fluid communication with the vaporizing chamber 910 through one or more conduits 909 to allow intake of air. Also shown in another conduit 907 between the chamber 910 and a suction opening 908 in a mouthpiece portion 906 of the head 904. A user may inhale vapor from the vaporizing chamber 910 through the suction opening 908.

Figure 91:
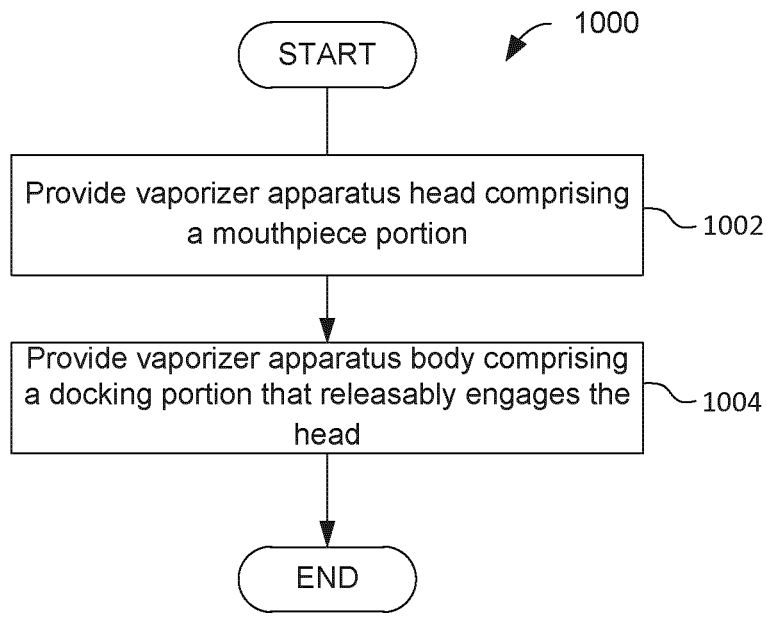
FIG. 91 is a flowchart of a method for making a vaporizer apparatus according to some embodiments.

FIG. 91 is a flow chart of a method 1000 for making a vaporizer apparatus according to some embodiments. At block 1002, a vaporizer apparatus head is provided that comprises a mouthpiece portion. The head may have any of the features of the example heads described above, and particularly with reference to FIGS. 1 to 58. At block 1004, a vaporizer apparatus body is provided that comprises a docking portion that releasably engages the head in at least one of an operational position and a non-operational position. In some embodiments, the docking portion at least partially receives the head in the operational position and the non-operational position. The head may be removable from the docking portion to be moved between the operational and non-operational positions. The body may have any of the features of the example bodies described above, and particularly with reference to FIGS. 1 to 58. The term "providing" in this context may refer to making, manufacturing, buying, or otherwise obtaining the head or body.

The method 1000 may further comprise docking the head with the body in either the operational or non-operational position. The method 1000 may further comprise moving the head from the operational position to the non-operational position (or vice versa). The method may further comprise placing a power source such as a battery in the body.

In some embodiments, providing the body comprises: providing an inner body portion and an outer housing. The method may further comprise slidably engaging the inner body portion to the outer housing. The inner body portion and the outer housing may have any of the features described above, particularly with reference to the embodiments shown in FIGS. 9 to 58.

Figure 92:
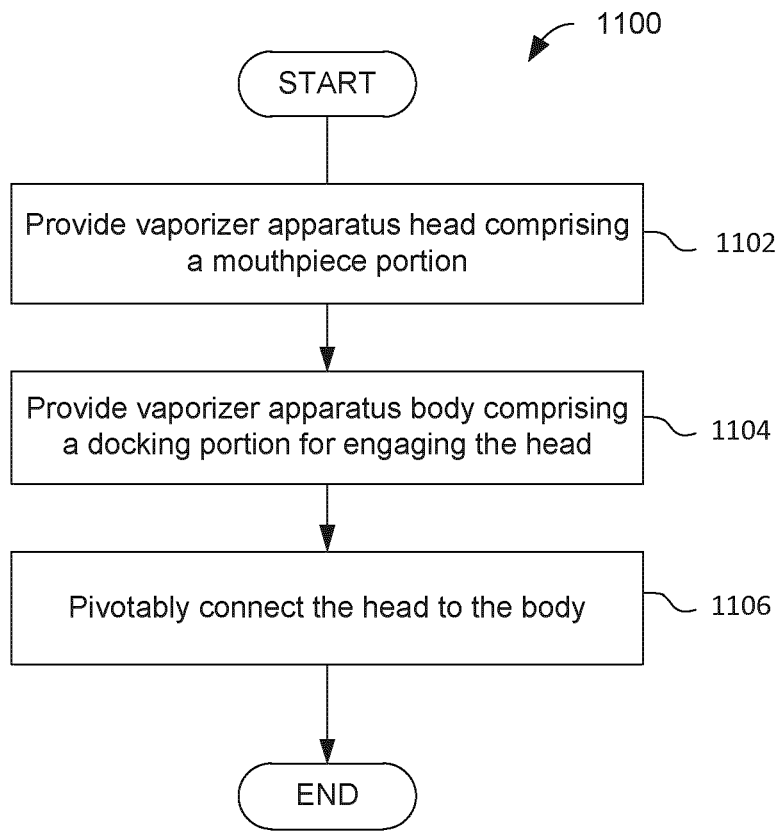
FIG. 92 is a flowchart of another method for making a vaporizer apparatus according to some embodiments.

FIG. 92 is a flow chart of a method 1100 for making a vaporizer apparatus according to some embodiments. At block 1102, a vaporizer apparatus head is provided that comprises a mouthpiece portion. The head may have any of the features of the example heads described above, and particularly with reference to FIGS. 59 to 89. At block 1104, a vaporizer apparatus body is provided that comprises a docking portion for engaging the head. The body may have any of the features of the example bodies described above, and particularly with reference to FIGS. 59 to 89. At block 1106, the head is pivotably connected to the body so that the head is movable between an operational position and a non-operational position. The head engages the body in one of the operational position and a non-operational position. The term "providing" in this context may refer to making, manufacturing, buying, or otherwise obtaining the head or body.

The method 1100 may further comprise engaging the head with the body in either the operational or non-operational position. The method 1100 may further comprise moving the head from the operational position to the non-operational position (or vice versa). The method may further comprise placing a power source such as a battery in the body.

In some embodiments, pivotably connecting the head and the body comprises connecting the head and body with a hinge.

It should be apparent to those skilled in the art that more modifications besides those already described are possible without departing from the inventive concepts herein. The inventive subject matter, therefore, is not to be restricted except in the scope of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly reference.

Although particular embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

It is to be understood that a combination of more than one of the approaches described above may be implemented. Embodiments are not limited to any particular one or more of the approaches, methods or apparatuses disclosed herein. One skilled in the art will appreciate that variations or alterations of the embodiments described herein may be made in various implementations without departing from the scope of the claims.

What is claimed is:

1. A vaporizer apparatus, comprising:
a body;
a head comprising a mouthpiece portion, the head being movable between an operational position and a non-operational position, and the head being engaged with the body in the operational and non-operational positions; and
a vaporizing chamber to receive a material and vaporizing means operatively coupled to the vaporizing chamber and operable to vaporize the material therein when activated, the vaporizing means being activatable when the head is in the operational position,
wherein the head is removable from the body, and the body comprises a docking portion and the head releasably engages the docking portion of the body in the operational position and the non-operational position, and wherein the docking portion comprises a docking bay that at least partially receives the head in the operational and non-operational positions,
wherein the mouthpiece portion of the head is received in the docking bay in the non-operational position, and the mouthpiece portion of the head extends away from the docking bay in the operational position, and the non-operational position of the head is axially reversed relative to the operational position.

2. The vaporizer apparatus of claim 1, wherein the body is elongate and has an end, wherein the docking portion is disposed in the end of the body.

3. The vaporizer apparatus of claim 1, wherein moving the head to the operational position enables activation of the vaporizing means, and moving the head out of the operational position disables the vaporizing means.

4. The vaporizer apparatus of claim 1, wherein, in the operational position, the mouthpiece portion of the head is exposed and accessible.

5. The vaporizer apparatus of claim 1, wherein the body comprises an outer housing and an inner body portion slidably received within the outer housing, and wherein the head abuts the inner body portion when received in the docking bay.

6. The vaporizer apparatus of claim 5, wherein the inner body portion is axially movable within the outer housing between a first longitudinal position and a second longitudinal position, the head being fully receivable into the docking bay in the first longitudinal position, and the head being partially ejected from the docking bay when the inner body portion is in the second longitudinal position.

7. The vaporizer apparatus of claim 6, further comprising at least one of: a first at least one biasing element that biases the head to remain the operational position; a second at least one biasing element that biases the head to remain the non-operational position; and a third at least one biasing element that biases the inner body portion to remain in the first or second longitudinal position.

8. The vaporizer apparatus of claim 7, wherein the at least one biasing element comprises at least one of: at least one magnet; or at least one spring.

9. The vaporizer apparatus of claim 1, wherein the head is collinear with the body in both the operational and non-operational positions.

10. The vaporizer apparatus of claim 1, wherein the body at least partially covers the mouthpiece portion of the head when the head is in the non-operational position.

11. The vaporizer apparatus of claim 10, wherein the head comprises a first one or more operative connectors, and the body comprises a second one or more operative connectors that engage the first one or more of the operative connectors to enable activation of the vaporizing means when the head is in the operational position.

* * * * *